US008138601B2

(12) United States Patent
Komatsu et al.

(10) Patent No.: US 8,138,601 B2
(45) Date of Patent: Mar. 20, 2012

(54) ULTRASONIC MEASURING METHOD, ELECTRONIC COMPONENT MANUFACTURING METHOD, AND SEMICONDUCTOR PACKAGE

(75) Inventors: Shinsuke Komatsu, Osaka (JP); Yoichiro Ueda, Osaka (JP)

(73) Assignee: Panasonic Corporation, Osaka (JP)

( * ) Notice: Subject to any disclaimer, the term of this patent is extended or adjusted under 35 U.S.C. 154(b) by 527 days.

(21) Appl. No.: 12/338,157

(22) Filed: Dec. 18, 2008

(65) Prior Publication Data

US 2009/0189278 A1 Jul. 30, 2009

(30) Foreign Application Priority Data

Dec. 26, 2007 (JP) ................................ 2007-333767
Dec. 15, 2008 (JP) ................................ 2008-318628

(51) Int. Cl.
*H01L 23/06* (2006.01)

(52) U.S. Cl. .................. 257/729; 73/627; 257/E23.191

(58) Field of Classification Search .................. 257/729, 257/E23.191; 73/627
See application file for complete search history.

(56) References Cited

FOREIGN PATENT DOCUMENTS

| | | |
|---|---|---|
| JP | 5-333007 | 12/1993 |
| JP | 6-294779 | 10/1994 |

*Primary Examiner* — Roy Potter

(74) *Attorney, Agent, or Firm* — Wenderoth, Lind & Ponack, L.L.P.

(57) ABSTRACT

The waveform signals of ultrasonic waves reflected by a plurality of interfaces in a measurement object are received, the waveform signal of a reflected wave on a reference interface inside the measurement object is detected based on the amplitudes of the received waveform signals, and evaluation is made on the bonded condition of an interface to be measured based on the waveform signal of the reflected wave on the reference interface.

7 Claims, 16 Drawing Sheets

23
70
TRANSMITTER CIRCUIT
71
RECEIVER CIRCUIT
72
A/D CIRCUIT
73
74
DATA CALCULATION UNIT
75
DETERMINATION UNIT
76
MASTER DATA RETAINING MEMORY
80
REFERENCE INTERFACE DETERMINATION UNIT
78
DRIVE CONTROL UNIT
MEASUREMENT POSITION DATA MEMORY
77
22
INPUT UNIT
24
DISPLAY UNIT
21
21a 25
25a
40
42
38
44
21
37
43
46
41
39
X
Z
Y

AMPLITUDE
100%
50%
0%
-50%
-100%
TIME
$t_0$
$t_1$
14
15

ULTRASONIC MEASURING METHOD, ELECTRONIC COMPONENT MANUFACTURING METHOD, AND SEMICONDUCTOR PACKAGE

BACKGROUND OF THE INVENTION

The present invention relates to an ultrasonic measuring method, an electronic component manufacturing method, and a semiconductor package, and in particular, to an ultrasonic measuring method directed to a measurement object of which a plurality of interfaces cross a direction of ultrasonic radiation, an electronic component manufacturing method for providing, as a product, an electronic component that have been measured and evaluated as being non-defective by the ultrasonic measuring method, and the semiconductor package for use in the ultrasonic measuring method.

Conventional apparatuses for measuring the interiors of objects include an ultrasonic measuring apparatus that performs measurement by means of ultrasonic waves emitted and reflected back from an internal portion of an object (see, e.g., Patent Document 1 (Japanese Unexamined Patent Publication No. 05-333007) and Patent Document 2 (Japanese Unexamined Patent Publication No. 06-294779)).

As a conventional ultrasonic measuring apparatus, an ultrasonic measuring apparatus for measuring the interior of a semiconductor package is described.

FIG. 11 is a schematic structural view of a conventional ultrasonic measuring method. X-, Y-, and Z-axes are indicated in the figures for clarifying the relative positional relationships among the figures.

In FIG. 11, an ultrasonic measuring apparatus 1 includes an ultrasonic probe 2 for emitting and receiving ultrasonic waves, an input unit 3 for inputting conditions for ultrasonic measurement, such as frequencies of ultrasonic waves to be transmitted, a control unit 4 for processing information acquired from the ultrasonic probe 2 and the input unit 3 to control the operation of the ultrasonic probe 2, and a display unit 5 for displaying results of measurement including ultrasonic waveforms.

The operation of the ultrasonic measuring apparatus 1 is briefly described.

Based on the conditions for measurement inputted at the input unit 3, ultrasonic waves that are emitted with the movement of the ultrasonic probe 2 controlled at the control unit 4 are applied onto a semiconductor package 7 through the medium of water 6 in a container. The reflected waves reflected back from the semiconductor package 7 serving as a measurement object are received at the ultrasonic probe 2. The received reflected waves are processed at the control unit 4 such that the semiconductor package 7 is determined whether it is defective or not and an image thereof is created, and the result is displayed at the display unit 5.

The ultrasonic probe 2 is used here both for emission and reception. The control unit 4 includes a pulser/receiver that converts the reflected waves received at the ultrasonic probe 2 into voltages for amplification, as well as an image processor that visualizes intensity values of the voltage waveforms.

The semiconductor package 7 is a package which has a multilayer structure along the direction of ultrasonic radiation (the Z-axis direction in FIG. 11) including a plurality of interfaces.

To describe the conventional ultrasonic measurement in further detail, the measuring part and areas therearound in FIG. 11 are enlarged and described along with the structure of the semiconductor package 7.

FIG. 12 is a schematic view of the conventional ultrasonic measurement.

In FIG. 12, the semiconductor package 7 includes a substrate 8 having substrate-side electrodes on its upper surface, solders 9 serving as examples of bonding members provided between the substrate 8 and the respective substrate-side electrodes, an interposer 10 having interposer-side electrodes bonded by the solders 9 to the substrate-side electrodes on the substrate 8, a semiconductor chip 11, lead wires 12 connecting the interposer 10 with the semiconductor chip 11, and a resin mold 13 covering the semiconductor chip 11.

As shown in FIG. 12, the semiconductor package 7 is sunk in water in the example shown here, wherein the semiconductor package 7 placed in a liquid (water) 6, which package serves as a specific example of a measurement object, has a plurality of interfaces formed therein, including an interface between the water 6 and the resin mold 13, an interface between the resin mold 13 and the interposer 10, and an interface between the interposer 10 and the solder 11.

In this structure, the ultrasonic waves from the ultrasonic probe 2 are applied onto the semiconductor package 7, and when the reflected waves back from the semiconductor package 7 are received at the ultrasonic probe 2, the signals thereof have a waveform in which a plurality of waves are overlapped with one another. The waveform is described.

In the case where the semiconductor package 7 with a plurality of interfaces as shown in FIG. 12 is subjected to ultrasonic measurement, a waveform shown in FIG. 13 is acquired.

FIG. 13 is a view illustrating an ultrasonic waveform acquired in the conventional ultrasonic measurement. A description is given on a method for determining defectiveness or non-defectiveness at a measurement location using the waveform.

As shown in FIG. 13, in the case where the semiconductor package 7 having a plurality of interfaces therein is measured, it is difficult to define a measurement location (interface) because a plurality of waves are overlapped with one another.

Hence, with a surface of the semiconductor package 7 that gives stable ultrasonic waveforms being set as a reference, a measurement location (interface) is defined by using time-delay (phase shifting) from the surface.

In FIG. 13, a trigger 14 (at time $t_0$) is provided on the time base with respect to surface waves from the surface of the semiconductor package 7. Subsequently, based on the internal structure of the semiconductor package 7, a time domain called a gate 15 (at time $t_1$) is set with the trigger 14 placed at a zero origin, with respect to the reflected waves at a measurement location. Then, comparison with a threshold value is made within the section (the time domain) of the gate 15 to evaluate the measurement location.

The method however entails an issue of degradation in accuracy of measurement in the case where serial ultrasonic measurement is performed on two semiconductor packages of the same kind. The issue is described.

FIG. 14 is a view illustrating waveforms of reflected ultrasonic waves acquired in the conventional ultrasonic measurement.

When two semiconductor packages of the same kind are subjected to serial ultrasonic measurement, waveforms shown in FIG. 14 are acquired. As shown in FIG. 14, the reflected waves from the two semiconductor packages, i.e., a reflected wave 16 from a first semiconductor package and a reflected wave 17 from a second semiconductor package, are acquired shifted on the time base.

According to the conventional ultrasonic measurement, a measurement location of the reflected wave 17 is evaluated by using a trigger 18 (at time $t_2$) and a gate 19 (at time $t_3$) that are set initially based on the reflected wave 16. Thus, as shown in FIG. 14, the gate 19 (at time $t_3$) deviates widely from the true measurement location (at time $t_4$) of the reflected wave 17.

SUMMARY OF THE INVENTION

In order to provide a highly accurate ultrasonic measuring method, electronic component manufacturing method, and semiconductor package even for a measurement object of which a plurality of interfaces cross a direction of ultrasonic irradiation, the present invention has a construction as follows.

According to a first aspect of the present invention, there is provided an ultrasonic measuring method comprising:

receiving at an ultrasonic probe waveform signals of ultrasonic waves reflected from a plurality of interfaces in a measurement object;

detecting by a calculation unit a waveform signal of a reflected wave on a reference interface in the measurement object based on amplitudes of the waveform signals received at the ultrasonic probe; and measuring by the calculation unit an interface to be measured of the measurement object, the interface to be measured being specified with the waveform signal of the reflected wave on the reference interface set as an origin.

According to a second aspect of the present invention, there is provided the ultrasonic measuring method according to the first aspect, wherein the measurement object is an electronic component, the interface to be measured is a portion inside the electronic component, the portion being at an electrode joint portion or a portion adjacent to the electrode joint portion at which electrodes are bonded with a bonding member, and the interface to be measured is measured by the calculation unit and then a bonded condition of the electrode joint portion at the interface to be measured is evaluated by the calculation unit.

According to a third aspect of the present invention, there is provided the ultrasonic measuring method according to the first or second aspect, wherein, in detecting the waveform signal, the reference interface is an interface that provides a maximum amplitude intensity among the plurality of interfaces in the measurement object.

According to a fourth aspect of the present invention, there is provided the ultrasonic measuring method according to any one of the first to third aspects, wherein, in detecting the waveform signal, the reference interface is a surface of a buried object buried in the measurement object.

According to a fifth aspect of the present invention, there is provided the ultrasonic measuring method according to any one of the first to fourth aspects, wherein, in detecting the waveform signal, the measurement object is a semiconductor package, the reference interface is a portion inside the semiconductor package, the portion being at an electrode joint portion or a portion adjacent to the electrode joint portion at which the electrodes are bonded with a bonding member, and located at an interface between two layers of different materials.

According to a sixth aspect of the present invention, there is provided the ultrasonic measuring method according to any one of the first to fifth aspects, wherein in receiving the waveform signals of the ultrasonic waves, received are ultrasonic waveform signals of the ultrasonic waves that are transmitted from the ultrasonic probe and reflected from the plurality of interfaces in the measurement object, and the method further comprising, after the detection of the waveform signal on the reference interface and before the measurement of the interface to be measured by the calculation unit, adjusting a position of the ultrasonic probe based on a waveform signal received with the ultrasonic probe and the measurement object being moved toward each other.

According to a seventh aspect of the present invention, there is provided the ultrasonic measuring method according to any one of the first to third aspects, wherein, in measuring the interface to be measured by the calculation unit, a waveform signal detected after the waveform signal of the reflected wave on the reference interface is compared with a preliminarily inputted waveform signal of a non-defective product with reference to the waveform signal of the reflected wave on the reference interface, and the interface to be measured is evaluated based on result of the comparison.

According to an eighth aspect of the present invention, there is provided an electronic component manufacturing method comprising:

measuring and evaluating an interface to be measured of an electronic component according to the ultrasonic measuring method defined in any one of the first to seventh aspects, with the measurement object being the electronic component; and providing, as a product, the electronic component evaluated as being non-defective.

According to a ninth aspect of the present invention, there is provided a semiconductor package comprising:

a substrate having on its upper surface a substrate-side electrode;

an interposer having on its lower surface an interposer-side electrode, the interposer being bonded to the substrate;

a bonding member for bonding the substrate-side electrode with the interposer-side electrode;

a semiconductor chip directly connected to the interposer; and a resin mold covering the semiconductor chip, wherein a reference interface that is capable of providing a waveform signal of an ultrasonic wave reflected upon being irradiated is a portion inside the semiconductor package, the portion being at an electrode joint portion or a portion adjacent to the electrode joint portion at which the electrodes are bonded with the bonding member, and located at an interface between two layers of different materials.

According to a 10th aspect of the present invention, there is provided the semiconductor package according to the ninth aspect, wherein the reference interface is located at an interface where two adjacent layers of different materials provide a maximum difference in acoustic impedance in comparison with a difference in acoustic impedance between other two layers.

BRIEF DESCRIPTION OF THE DRAWINGS

These and other aspects and features of the present invention will become clear from the following description taken in conjunction with the preferred embodiments thereof with reference to the accompanying drawings, in which.

DETAILED DESCRIPTION OF THE EMBODIMENTS

Figure 1A:
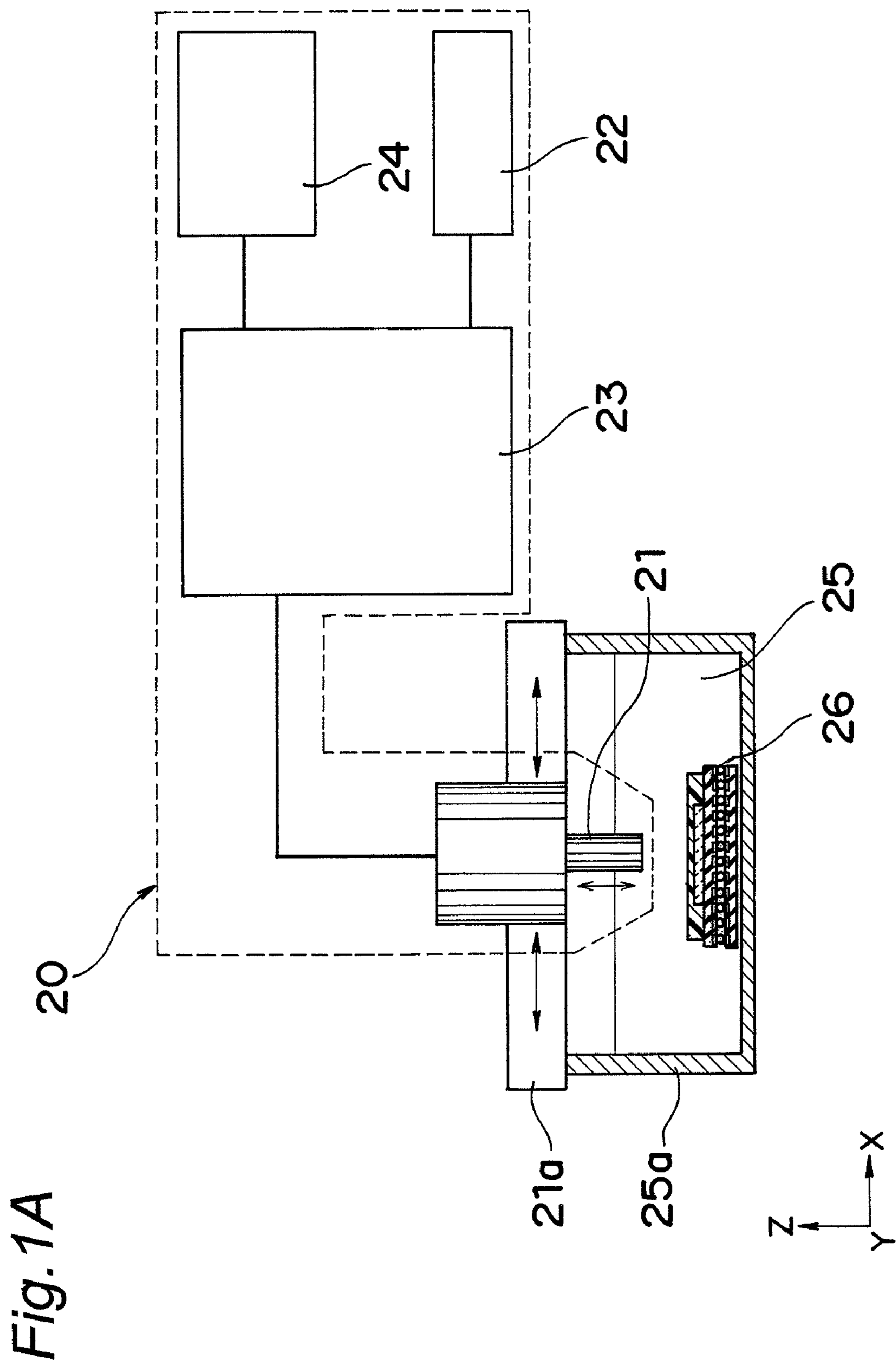
FIG. 1A is a schematic structural view of an ultrasonic measuring apparatus for implementing an ultrasonic measuring method according to a first embodiment of the present invention.

Before the description of the present invention proceeds, it is to be noted that like parts are designated by like reference numerals throughout the accompanying drawings.

Embodiments of the present invention are described below with reference to the drawings. Described as an apparatus and a method for ultrasonic measurement according to the present invention are an apparatus and a method for ultrasonic measurement by which the interior of an electronic component that serves as a measurement object, e.g., a semiconductor package, is measured.

First Embodiment

FIG. 1A is a schematic structural view of an ultrasonic measuring apparatus for implementing an ultrasonic measuring method according to a first embodiment of the present invention.

In FIG. 1A, the ultrasonic measuring apparatus 20 includes an ultrasonic probe 21 for emitting and receiving ultrasonic waves, an ultrasonic probe drive unit 21*a* for driving the ultrasonic probe 21 independently in mutually orthogonal X-, Y-, and Z-axes directions, an input unit 22 for inputting conditions for ultrasonic measurement, a control unit 23 for processing the information acquired from the ultrasonic probe 21 and the input unit 22 to control the operation of the ultrasonic probe 21, and a display unit 24 serving as an example of an output unit for displaying results of measurement including ultrasonic waveforms.

The operation of the ultrasonic measuring apparatus 20 is briefly described.

The lower end of the ultrasonic probe 21 is disposed in water 25 in a water tank 25*a*, and a semiconductor package 26 serving as an example of a measurement object is disposed at a predetermined position for disposing the measurement object in the water 25 in the water tank 25*a*. Ultrasonic waves with a frequency band of, e.g., about 10 to 100 MHz can be applied onto the semiconductor package 26 through the medium of the water 25 so as to receive the reflected waves back from a plurality of interfaces in the semiconductor package 26.

In FIG. 1A, directions that extend along a plane parallel to the bottom surface of the water tank 25*a* and are orthogonal to each other are defined as X and Y directions, and a direction orthogonal to the plane set by these directions is further defined as a Z direction.

The ultrasonic probe drive unit 21*a* is constructed by, for example, an XYZ robot that causes the ultrasonic probe 21 to move in each of the X, Y, and Z directions. The ultrasonic probe 21, the ultrasonic probe drive unit 21*a*, a transmitter circuit 70 to be described later, and a receiver circuit 71 to be described later constitute an example of an ultrasonic transmission/reception apparatus.

The control unit 23 is connected with the ultrasonic probe 21, the input unit 22, and the display unit 24.

Figure 15A:
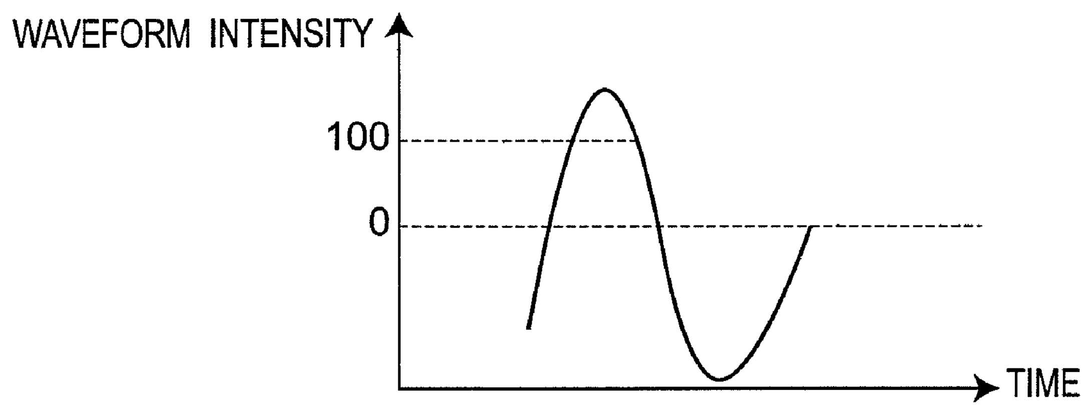
FIG. 15A is a graph showing a case in which a threshold value that serves as a criterion for determining defectiveness or non-defectiveness in the operation of the ultrasonic measurement according to the first embodiment is exceeded by a maximum value of waveform intensity, resulting in determining as non-defectiveness.
Figure 15B:
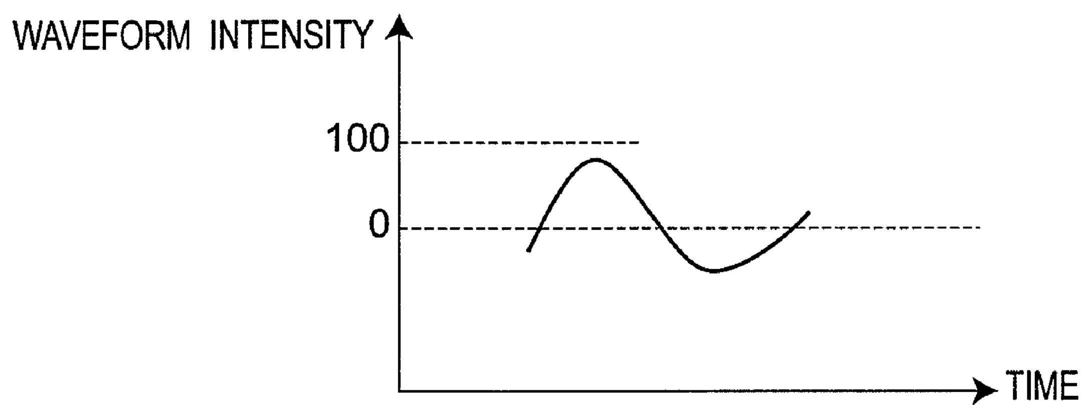
FIG. 15B is a graph showing a case in which a maximum value of waveform intensity is smaller than the threshold value that serves as the criterion for determining defectiveness or non-defectiveness in the operation of the ultrasonic measurement according to the first embodiment, resulting in determining as defectiveness.

The input unit 22 is a device that an operator uses to input information necessary for ultrasonic measurement, such as numerical values, using various input devices such as a keyboard, a mouse, a touch panel, or an audio input device, or to input information necessary for ultrasonic measurement, such as CAD data of the semiconductor package 26 (including, e.g., the material, thickness, dimensions of sides, and acoustic impedance of each layer of the semiconductor package or the substrate, the position of a semiconductor chip, and the positions of joint portions), position coordinates data of the position at which the semiconductor package 26 is disposed in the water tank, and conditions for ultrasonic irradiation (including an aperture, focal distance, and power). The input unit 22 further includes connection terminals with a database such as an additional server or a recording medium, for storing data on a measurement position data memory 77, a determination unit 75, and a master data retaining memory 76 (and further on a reference interface determination unit 80 to be described later). Inputted from the input unit 22 are, e.g., conditions for measurement to be stored on the measurement position data memory 77, the determination unit 75, and the master data retaining memory 76. That is, information required for a drive control unit 78 is inputted from the input unit 22 to be stored on the measurement position data memory 77. Information required for the determination unit 75 is inputted from the input unit 22 to be stored on an internal memory of the determination unit 75. Information required for a data calculation unit 74 is inputted from the input unit 22 to be stored on the master data retaining memory 76. Examples of the conditions for measurement include a scan area, a scan pitch, a trigger position, a trigger width, a gate position, a gate width, and the like. As to which area of the semiconductor package 26 is measured is set as the scan area (a measured portion, i.e., a portion to be measured) of the ultrasonic probe 21 (in other words, the position of an X-Y plane and a position in the Z direction are set). For example, the scan area may be the entire surfaces of the semiconductor package 26, or a portion of the semiconductor package 26, or may be set at a plurality of areas within the semiconductor package 26. The scan pitch means a mechanical resolution (for the X-Y plane) for acquiring waveform data (waveform signals) of reflected waves. For example, data may be acquired at a pitch of several micrometers to 100 micrometers, but the present invention is not limited thereto. The trigger position, trigger width, gate position, and gate width relate to a signal (a trigger signal) for designating a reference position in a measurement time signal as well as to a measurement starting position signal (a gate signal) that is temporally offset from the reference signal. The setting of the trigger position is important in the first embodiment; the trigger position being set at, as will be described later in further detail, e.g., a characteristic portion inside the semiconductor package 26 (an interface located at an electrode joint portion or a portion close to the electrode joint portion, between layers of substances that are greatly different from each other in acoustic impedance). The trigger width is set approximately equal to the wavelength of the ultrasonic probe to be used. For example, in the case of an ultrasonic probe capable of transmitting an ultrasonic wave of, e.g., 100 MHz, one wavelength is 10 ns, and assuming that the actual wave number of the ultrasonic wave outputted from the ultrasonic probe is 1.5 wavelengths, the trigger width may be 15 ns. As for the setting of the gate position, it is conceivable that the gate position is set by the data calculation unit 74, which is an example of a calculation unit, based on predefined master data. The gate width is typically set by the data calculation unit 74 to the width of a reflected wave in a focused time zone, and in many cases, is set by the data calculation unit 74 to the length corresponding to one cycle of a sine wave or shorter. The frequency band of the ultrasonic wave used for the semiconductor package 26 is from about 10 to 100 MHz; therefore, the gate width is set by the data calculation unit 74 from 10 to 100 ns in many cases. A plurality of numbers of gates are set for comparison with other gate information in the case where information on an interface to be measured is missing. Defectiveness or non-defectiveness is determined on a measured portion (e.g., the electrode joint portion) of the semiconductor package 26, as will be described later, primarily based on values of waveform intensity within the sections of the gates thus set. According to an example of the defectiveness or non-defectiveness determining method, it is possible to determine defectiveness or non-defectiveness by using the maximum value and the minimum value (the negative maximum value) of waveform intensity within the section of a gate or by using the maximum value of the absolute value, to compare the values with a threshold value indicating a good bonded condition. According to a specific example of the defectiveness or non-defectiveness determining method, a value for determining "OK/NG" (defectiveness or non-defectiveness) is set in advance for use as the threshold value. For example, in FIGS. 15A and 15B, the threshold value is set to 100, and if the maximum value exceeds the threshold value, "OK" (non-defectiveness) is determined, whereas if the maximum value is below the threshold value, "NG" (defectiveness) is determined. The threshold value is decided through measurement on actual defective products.

At a pre-stage (a stage before starting measurement) for performing the following measurement steps, for example, information on conditions (including a temporal position at which measurement is started and a duration) of waveform master data is inputted from the input unit 22 to be stored on the master data retaining memory 76, thereby predefining waveform master data in the master data retaining memory 76. The master data needs to be provided with a certain amount of duration, in consideration of accuracy of sonic speed or/and variation in thickness of each layer. For example, the duration is 15 ns. The duration of the master data is decided depending on the frequency band of the ultrasonic probe to be used. How to decide the duration depends on the length (10 ns) of one wavelength in a frequency band (e.g., 100 MHz), and a setting duration (15 ns) is preferably further decided depending on the wave number of the actually outputted ultrasonic wave (1.5 wavelength).

The display unit 24 is constructed by, as one example, a display on which visualized results of determination are displayed after predetermined calculation and determination is made based on the information received at a data processing unit 73 to be described later of the control unit 23.

The control unit 23 includes the transmitter circuit 70 connected to the ultrasonic probe 21 to emit ultrasonic waves, the pulser/receiver (receiver circuit) 71 connected to the ultrasonic probe 21 to convert the ultrasonic waves received at the ultrasonic probe 21 into voltages for amplification, an A/D circuit 72 connected to the receiver circuit 71 to convert the signals of the received reflected waves into digital information, and the data processing unit 73 that receives the digital information from the A/D circuit 72 to perform predetermined data processing (e.g., visualization of intensity values of the measured waveforms). The control unit 23 further includes the measurement position data memory 77 as well as the drive control unit 78 respectively connected to the ultrasonic probe drive unit 21*a* and the measurement position data memory 77 to drive and control the ultrasonic probe drive unit 21*a* based on the information stored on the measurement position data memory 77.

The data processing unit 73 includes the master data retaining memory 76 serving as an example of a reference signal storage unit that preliminarily stores the master data to become a reference signal for waveform signals of ultrasonic reflected waves, the data calculation unit 74 serving as an example of a calculation unit that is connected to the master data retaining memory 76 and the A/D circuit 72 to perform calculations based on the information stored on the master data retaining memory 76 and the digital information from the A/D circuit 72, and the determination unit 75 connected to the data calculation unit 74 to perform an operation of determining defectiveness or non-defectiveness based on the results of the calculations at the data calculation unit 74.

Based on the conditions for measurement that have been inputted at the input unit 22, with the movement of the ultrasonic probe 21 controlled under the drive and control by the transmitter circuit 70 and the drive control unit 78 of the control unit 23, the ultrasonic waves emitted from the ultrasonic probe 21 are applied onto the semiconductor package 26 through the medium of the water 25. Then, the reflected waves back from the semiconductor package 26 serving as a measurement object are received at the ultrasonic probe 21. The received reflected waves are processed at the control unit 23 to determine whether or not the semiconductor package 26 is defective or not and an image thereof is created, whereon the result is displayed at the display unit 24. That is, the received ultrasonic signals are converted to voltages and amplified at the receiver circuit 71 of the control unit 23 based on the received information, are converted into digital information at the A/D circuit 72, and are inputted to the data calculation unit 74 of the data processing unit 73. The data calculation unit 74 performs waveform processing, image processing, and the like, so that the determination unit 75 determines defectiveness or non-defectiveness of interfaces in the semiconductor package 26 and visualizes the result of the determination. The visualized result of the determination is displayed on the display serving as an example of the display unit 24.

The ultrasonic probe 21 is simplified in the entire structure by using one ultrasonic probe both for emission and reception.

The semiconductor package 26 has a multilayer structure along the direction of ultrasonic irradiation (the Z-axis direction in the figure), is a package having a plurality of interfaces, and serves as an object to be measured (a measurement object) that is subjected to measurement as to the bonded conditions of border surfaces of its plurality of interfaces by means of detection of the waveform signals of reflected waves generated upon irradiation of ultrasonic waves.

Figure 2:
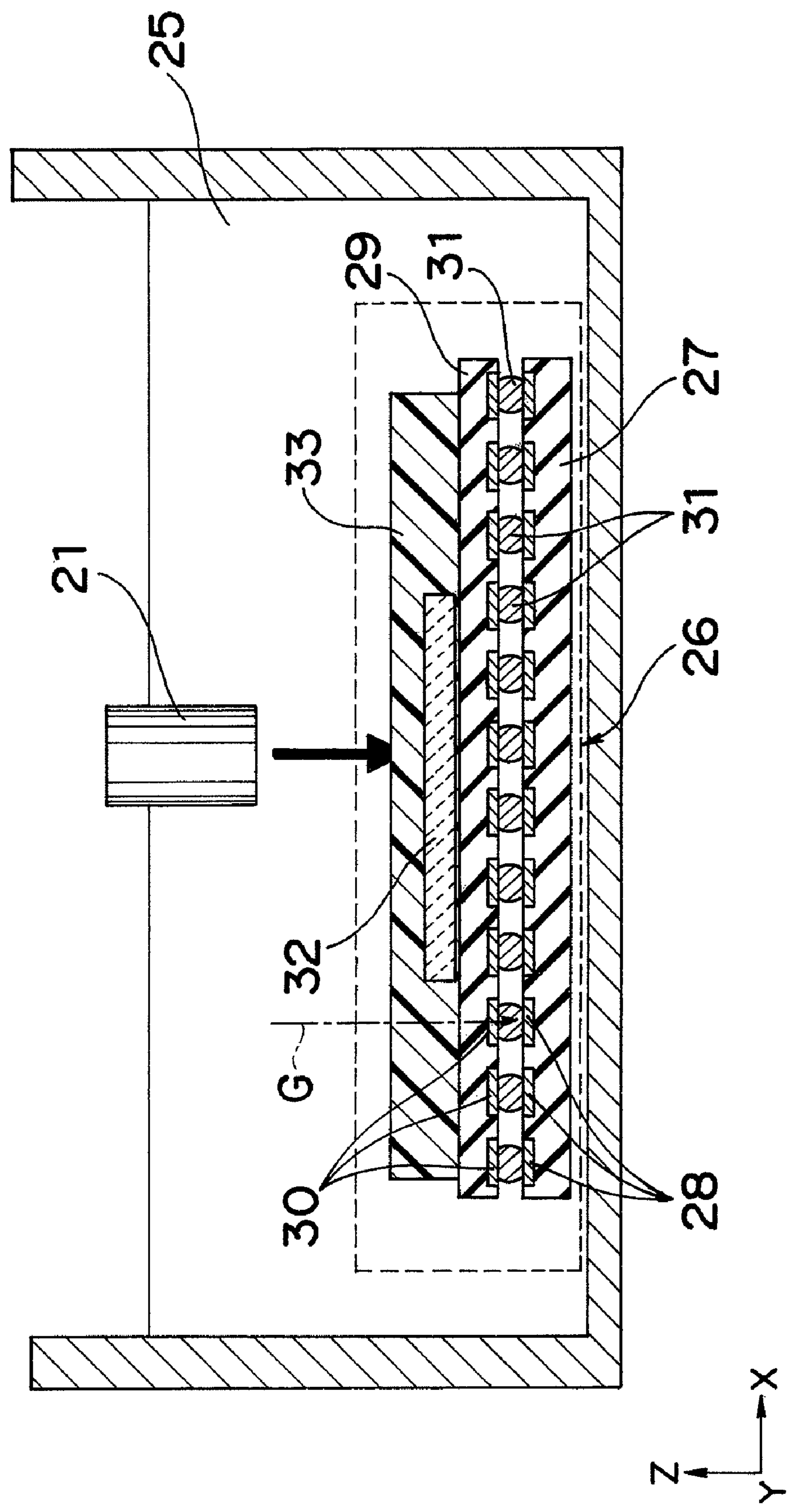
FIG. 2 is an explanatory view showing an operation of ultrasonic measurement according to the first embodiment.

The specific multilayer structure of the semiconductor package 26 is shown in FIG. 2. Ultrasonic waves are transmitted through the interior of the semiconductor package 26 as well, so that reflected waves are generated also from the internal interfaces. Thus, the signals of the reflected waves received at the ultrasonic probe 21 form waveform signals in which a plurality of waves generated from the plurality of interfaces are overlapped with one another.

In order to describe the ultrasonic measurement according to the first embodiment in further detail, the measured portion (the portion to be measured) and areas therearound in FIG. 1A are enlarged and described along with the structure of the semiconductor package 26.

In FIG. 2, the semiconductor package 26 is constructed by, for example, a substrate 27, substrate-side pads 28 provided on the upper surface of the substrate 27, an interposer 29 bonded with the substrate 27, interposer-side pads 30 provided on the lower surface of the interposer 29, solders 31 serving as an example of the bonding members for bonding the substrate-side pads 28 with the interposer-side pads 30, a semiconductor chip 32 directly connected to the interposer 29 by means of flip chip connection (not shown) or the like, and a resin mold 33 covering the semiconductor chip 32.

The semiconductor package 26 is manufactured in the following manner.

The semiconductor chip 32 is connected to the upper surface of the interposer 29 having a number of interposer-side pads 30 on its lower surface, by means of flip chip connection or the like.

Then, the semiconductor chip 32 on the interposer 29 is covered with an insulating synthetic resin to form the resin mold 33.

After that, the solders 31 are provided either on the interposer-side pads 30 on the interposer 29 or the substrate-side pads 28 on the substrate 27.

Subsequently, the interposer-side pads 30 on the interposer 29 are each connected to the substrate-side pads 28 on the substrate 27 with the solders 31 placed therebetween.

Through such a manufacturing process, an interface capable of functioning as a reference interface (a reference surface for determining defectiveness or non-defectiveness of a joint portion), as will be described later, is formed at the time of manufacturing. That is, a reference interface that reflects radiated ultrasonic waves so as to be able to provide ultrasonic waveform signals is located at a portion inside the semiconductor package 26, at the electrode joint portion or the portion adjacent to the electrode joint portion where electrodes (a pad 28 on the substrate side and a pad 30 on the interposer side) are bonded with the solders 31, and is an interface between two layers of different materials. Specifically, for example, the materials of the interposer 29 and of the interposer-side pads 30 are selected and used so that the difference in acoustic impedance between the interposer 29 and the interposer-side pads 30 is maximal in comparison with the differences in acoustic impedance between other two layers. More specifically, as will be described later, an epoxy resin may be used as a material of the interposer 29, and copper may be used as a material of the interposer-side pads 30.

An epoxy resin is used as a material of the substrate 27, copper (Cu) is used as materials of the substrate-side pads 28 and of interposer-side pads 30, and an epoxy resin is used as a material of the interposer 29. Materials of the solder 31 are a solder alloy such as Sn/Pb/Cu or Sn/Pb/Ag or a lead-free solder such as Sn/Ag/Cu or Sn/Cu. Si is used as a material of the semiconductor chip 32, and a mixture of an epoxy resin and a filler ($SiO_2$) is used as a material of the resin mold 33. Used as an example of the semiconductor package 26 of the first embodiment is a CSP package in which the package size and the silicon size are the same.

The substrate 27 has a thickness of several hundreds of micrometers and an internal sonic speed of 2500 m/s. Each of the substrate-side pads 28 and the interposer-side pads 30 has a thickness of several tens of micrometers and an internal sonic speed of 4700 m/s. The interposer 29 has a thickness in the range of 100 to 300 μm and an internal sonic speed of 2500 m/s. The solder 31 has a thickness of 100 μm and an internal sonic speed of 3200 m/s. The semiconductor chip 32 has a thickness in the range of 200 to 300 μm and an internal sonic speed of 8500 m/s. The resin mold 33 has a thickness in the range of 400 to 700 μm and an internal sonic speed of 3930 m/s. The above-mentioned values of the sonic speeds of ultrasonic the trigger (the reference signal) is set should be on the side of the ultrasonic probe 21 from the joint portions between the solders 31 and the substrate-side pads 28 on the substrate 27, which joint portions are finally measured portions. This is because the trigger needs to be gauged prior to the measured portion (the joint portions between the solders 31 and the substrate-side pads 28 on the substrate 27) in order to measure the measured portion based on the time-delay (phase shifting) from the trigger.

A method of setting the trigger is first described. Actually, the method of setting the trigger is performed, for example, in step S2 to be described later.

The trigger needs to have larger signal intensity than the waveforms therearound for its purpose of use. In order for an ultrasonic reflected waveform to have large intensity (amplitude intensity), the two materials of the interface need to have large difference in acoustic impedance. Where the acoustic impedances of two substances are $Z_1$ and $Z_2$, the reflection coefficient R of sound pressure is expressed as $R=(Z_2-Z_1)/(Z_2+Z_1)$. According to this relation, a reflected wave on an interface between layers of substances that are widely different in acoustic impedance from each other should be set as the trigger.

As a result of consideration from various aspects by the present inventors, in the first embodiment, an epoxy resin is used as the material of the interposer 29 and copper is used as the material of the interposer-side pads 30. Accordingly, the acoustic impedance of the epoxy resin is in the range of 2.9 to 3.6, and the acoustic impedance of copper is 45.8 (the unit of impedance is 10 kg/ms hereinafter). In the structure of the first embodiment, since the difference in acoustic impedance between these two layers (the interposer 29 and the interposer-side pads 30) is maximal of the respective differences in acoustic impedance between other two layers, a signal on this interface is set as the trigger. To further enhance the accuracy, it is possible to define as follows, rather than simply setting as the reference interface an interface between two layers that provides maximum difference in acoustic impedance of the differences in acoustic impedance between other two layers. May be defined as the reference interface an interface where difference in acoustic impedance between two layers is larger than a predetermined threshold value, which interface also has a larger area than that of the aperture of the ultrasonic waves to be emitted and is located at the joint portion, i.e., proximate to an interposer-side pad 30 or a substrate-side pad 28. If the difference in acoustic impedance is not larger than the predetermined threshold value, a reference interface may be formed in advance by applying second and third embodiments to be described later. An example of the condition for setting the reference interface may be such that, since the acoustic impedance of the epoxy-based resin is in the range of 2.9 to 3.6 and the acoustic impedance of metal (e.g., Cu or Ag) used for the reference interface is in the range of about 20 to 50, an interface with a difference in impedance of not less than 10 may be used as the reference interface.

Figure 1B:
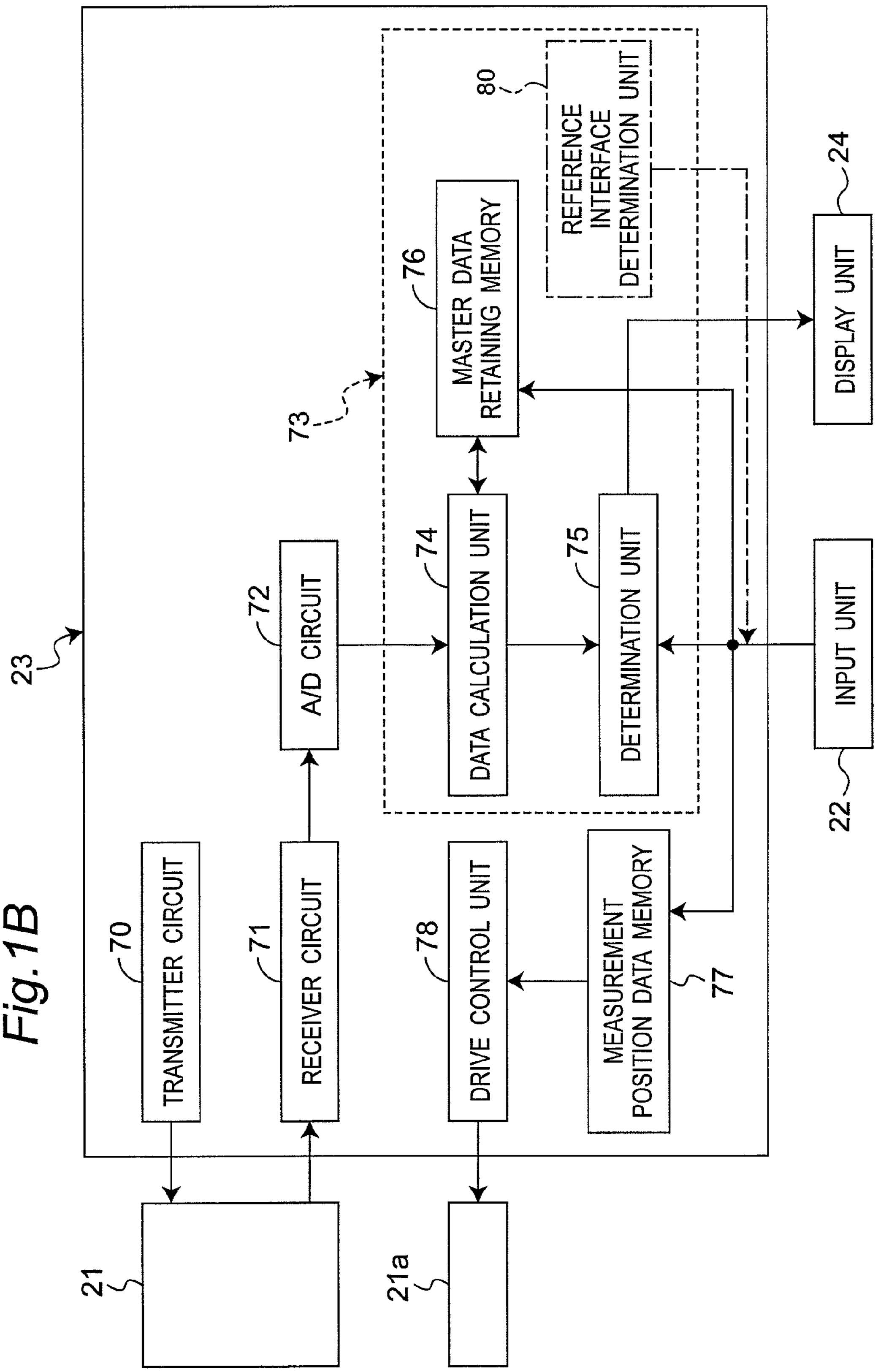
FIG. 1B is a block diagram of a control unit and the like of the ultrasonic measuring apparatus according to the first embodiment.

The reference interface determination unit 80 may be provided in the control unit 23 (see FIG. 1B) as a means for setting the reference interface as described above, so as to calculate difference in acoustic impedance between each two layers for comparison with one another and to determine an interface that has the maximum difference as the reference interface. Alternatively, the reference interface determination unit 80 may determine whether there is a reference interface formed in advance, and if there is the reference interface, the reference interface may be used, whereas if there is not the reference interface, differences in acoustic impedance between each two layers may be calculated for comparison with one another to determine the interface with the maximum difference as a reference interface. The information on the result determined at the reference interface determination unit 80 may be outputted to the measurement position data memory 77, the determination unit 75, and the master data retaining memory 76 to be stored thereon.

Figure 3:
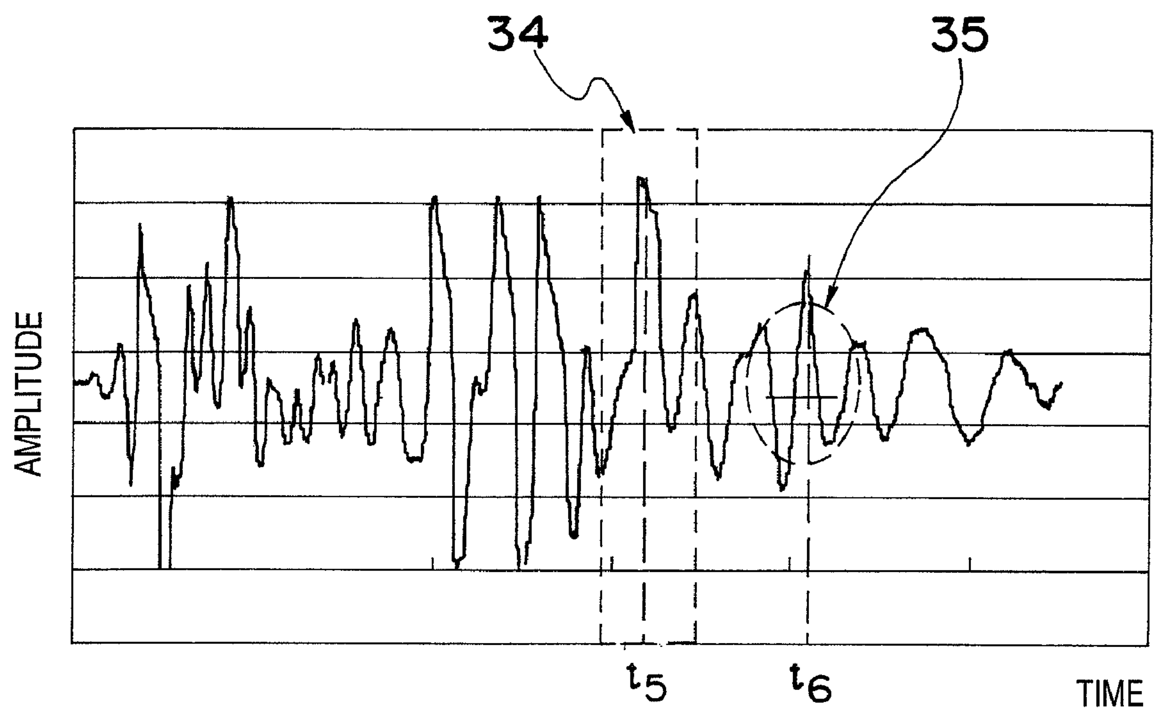
FIG. 3 is a view illustrating an ultrasonic waveform acquired in an ultrasonic measurement according to the first embodiment.

FIG. 3 is a view illustrating an ultrasonic waveform acquired in the ultrasonic measurement according to the first embodiment where the transverse axis indicates the time and the vertical axis indicates the amplitude.

In FIG. 3, a signal on the interface between the interposer 29 and the interposer-side pad 30 is set as a trigger 34 (at time $t_5$), and the position of a gate 35 (at time $t_6$), which is a signal of a measured portion, is specified from the trigger 34 by the data calculation unit 74. In the first embodiment, as a result of calculation for the time of occurrence at the data calculation unit 74 based on the thicknesses and sonic speeds of the respective constituents, it is found that the waveform of a signal (the gate 35) of an interface between the solder 31 and the substrate-side pad 28 on the substrate 27 occurs after 31 nsec from the occurrence of the trigger 34.

Employed as a method of evaluating the waveform intensity at the gate 35 is a method in which the position of the gate 35 is specified by the data calculation unit 74 using the time difference (phase difference) between the trigger 34 (the reference interface) and the gate 35 (the interface to be measured) that are found by the data calculation unit 74 based on the structure within the semiconductor package 26 in the above-described manner, and a threshold value that has been inputted in advance from the input unit 22 is compared at the data calculation unit 74 with the amplitude intensity of the waveform signal at this position, so that the interface to be measured (e.g., a joint surface) is evaluated (determined) at the determination unit 75 whether the interface is defective or not. That is, if the amplitude intensity of the waveform signal is smaller than the threshold value, it is determined as defectiveness by the determination unit 75. If the amplitude intensity of the waveform signal is larger than or equal to the threshold value, it is determined as non-defectiveness by the determination unit 75.

A description is given on an evaluating method other than the above-described evaluating method conducted through comparison with a threshold value.

Figure 4:
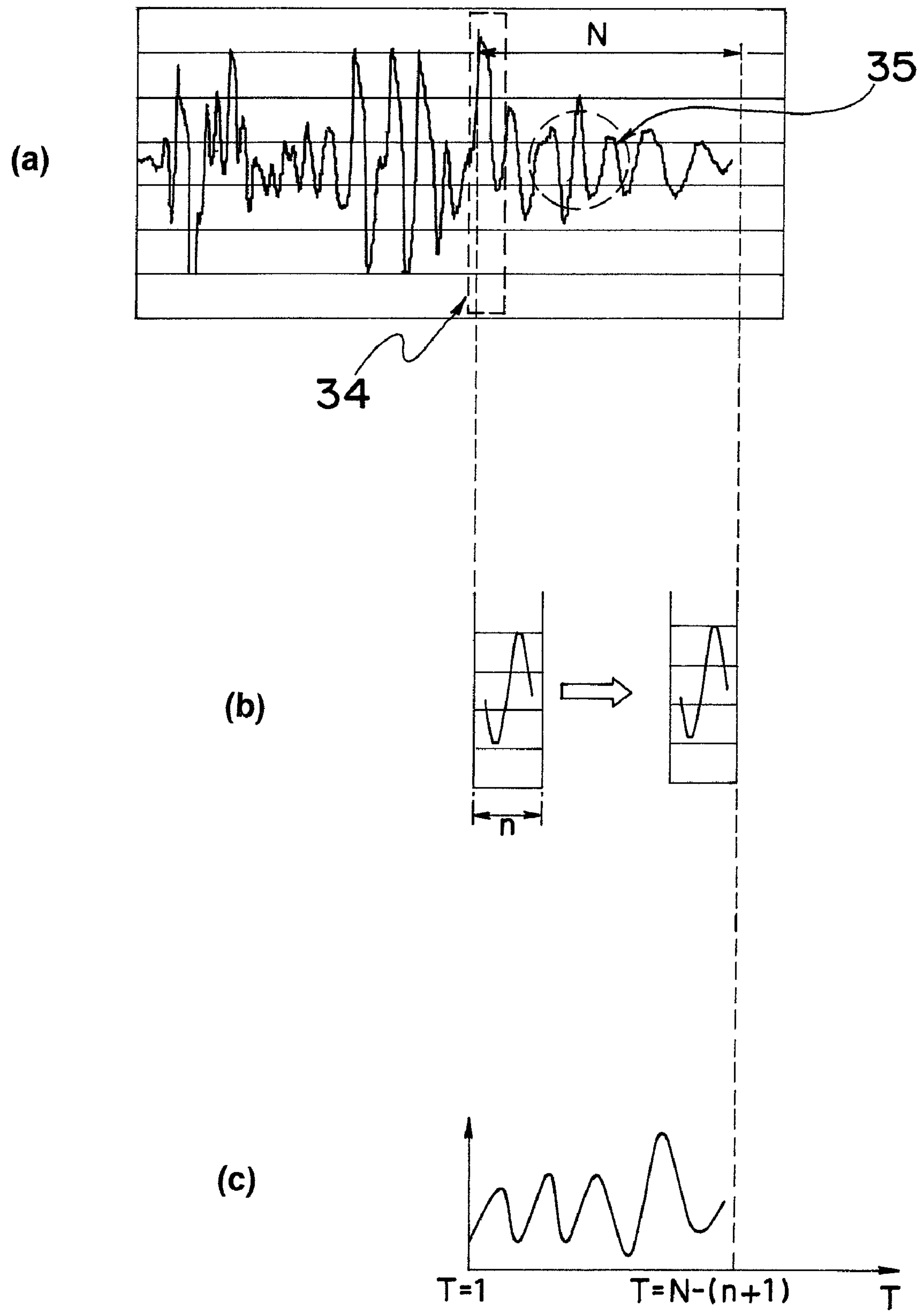
FIG. 4 is an explanatory view for describing an operation of evaluating waveform intensity at a gate position in the ultrasonic measurement according to the first embodiment, wherein (a) is a view illustrating evaluation of waveform intensity at the gate position in the ultrasonic measurement according to the first embodiment (the vertical axis indicates the amplitude and the transverse axis indicates the time), (b) is a view illustrating one cycle of master data in the ultrasonic measurement according to the first embodiment (the vertical axis indicates the amplitude and the transverse axis indicates the time), and (c) is a view illustrating values of coefficients of correlation in the ultrasonic measurement according to the first embodiment (the vertical axis indicates the amplitude and the transverse axis indicates the time)

The part (a) of FIG. 4 is a view illustrating evaluation of waveform intensity at a gate position in ultrasonic measurement according to the first embodiment, the part (b) of FIG. 4 is a view illustrating one cycle of master data used in the ultrasonic measurement according to the first embodiment, and the part (c) of FIG. 4 is a view illustrating values of coefficients of correlation in the ultrasonic measurement according to the first embodiment.

Employed as a method of evaluating waveforms according to the first embodiment is a method in which a waveform of a joint portion known to be non-defective between the solder 31 and the substrate-side pad 28 on the substrate 27 is cut out by the data calculation unit 74, is stored in advance on the master data retaining memory 76 as master data, and a function of correlation (the values of coefficients of correlation) between the master data and actually measured data (the digital information from the A/D circuit 72) is evaluated by the data calculation unit 74.

First, the temporal position of the trigger 34 is set as an origin T=1 at the data calculation unit 74. According to a procedure described below, an interface to be measured of the semiconductor package 26, the interface being specified with the waveform signal at the trigger 34 (the reference interface) set as the origin, is measured at the data calculation unit 74.

Subsequently, as shown in the part (b) of FIG. 4, a data column of coefficients of correlation relative to the measured data is formed at the data calculation unit 74 while shifting the master data in the time base direction (to the right on the paper plane of FIG. 4), at the data calculation unit 74.

Next, at the data calculation unit 74, the value of a coefficient of correlation is taken with the origins (T=1) of the measured data and of the master data aligned to each other.

Then, at the data calculation unit 74, the value of a coefficient of correlation is taken with the origin of the master data aligned to T=2, i.e., a second point of the measured waveform. This step is repeated at the data calculation unit 74 to T=N−(n+1) where the length of the measured data from the trigger 34 is N and the length of one cycle of the master data is n (providing N>n), and coefficients of correlation are calculated at each T to form a data column of coefficients of correlation shown in the part (c) of FIG. 4 at the data calculation unit 74.

Figure 5:
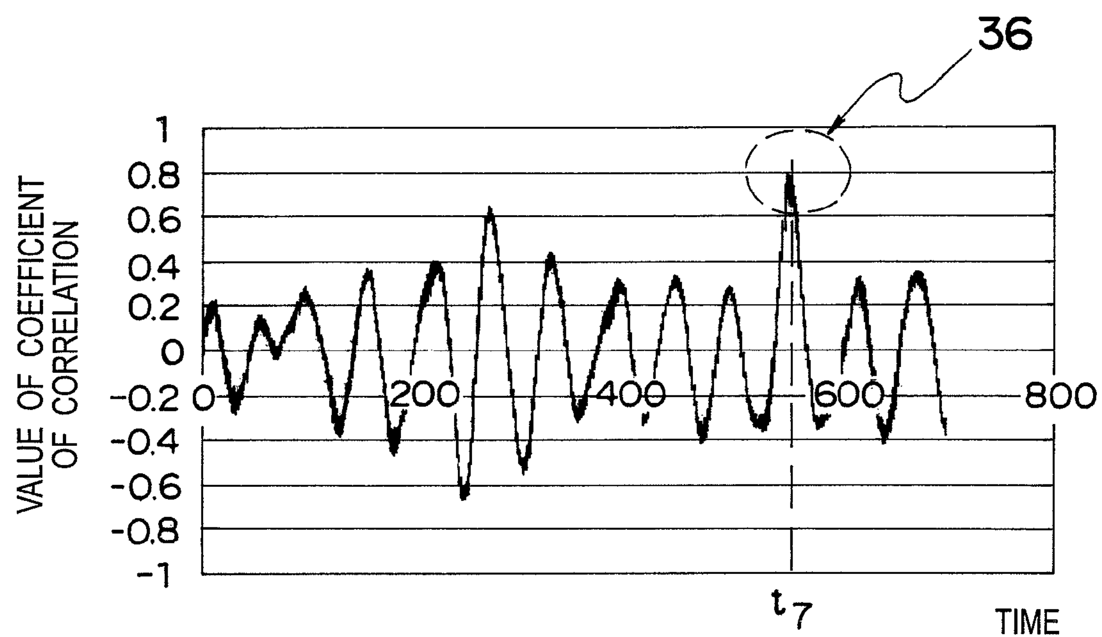
FIG. 5 is a view illustrating a data column of the coefficients of correlation in the ultrasonic measurement according to the first embodiment, detailing the part (c) of FIG. 4 (the vertical axis indicates the value of coefficient of correlation and the transverse axis indicates the time)

FIG. 5 is a view illustrating the data column of coefficients of correlation of the ultrasonic measurement according to the first embodiment, showing the part (c) of FIG. 4 in detail.

In FIG. 5, the transverse axis indicates the time T, and the vertical axis indicates the value of coefficient of correlation. At the data calculation unit 74, the value of a coefficient of correlation at the time when the master data and the measure data coincide with each other in the waveform of the joint portion is set as a maximum value point 36 (at time $t_7$) of the data column of coefficients of correlation, and the value of the coefficient of correlation at this maximum value point 36 is determined as waves fluctuate depending on the temperature of the measured article; therefore, in the first embodiment, it is assumed that the temperature is maintained constantly to a temperature satisfying the above-mentioned sonic speed values. A temperature measuring unit (not shown) may be used to measure the temperature of the measured article and to correct the sonic speeds, thereby providing even more accurate measurement.

As shown in FIG. 2, a plurality of interfaces are formed, including an interface between the water 25 and the resin mold 33, an interface between the resin mold 33 and the interposer 29, and interfaces between the interposer-side pads 30 and the solders 31.

A description is made on ultrasonic measurement that uses the above-described structure.

In the semiconductor package 26 as used in the first embodiment, variation in time-delay (phase shifting) has a significant influence in such a method as has been used conventionally of setting a trigger on a surface of the resin mold 33. Thus, a trigger (a reference signal or a reference interface) is first set at a portion other than the surface of the resin mold 33 by the data calculation unit 74 (or by the reference interface determination unit 80 and the data calculation unit 74).

In this case, the position of the interface where an evaluated value.

If the joint portion between the solder 31 and the substrate-side pad 28 on the substrate 27 is in a normally bonded condition, the measured data has a waveform close to that of the master data, and the value of the coefficient of correlation is close to 1. Contrarily, if the joint portion between the solder 31 and the substrate-side pad 28 on the substrate 27 is not in a favorably bonded condition with a crack or void generated therein, the value of the coefficient of correlation is smaller than 1.

According to the determining method using such coefficients of correlation, since the master data conventionally needs to be shifted in the time base direction relative to the entire measured data, the calculation time increases, and the master data is erroneously recognized for portions other than the joint portions. However, as in the first embodiment, a trigger is set by the data calculation unit 74 and the data calculation unit 74 performs processing relating to the coefficient of correlation based on the position of the trigger, whereby the calculation time is cut and the possibility of erroneous recognition is reduced advantageously.

In this manner, not a surface of the semiconductor package 26 but a characteristic portion inside the semiconductor package 26 (an interface at the electrode joint portion or the portion close to the electrode joint portion between layers of substances that are widely different from each other in acoustic impedance) is set as the trigger 34 by the data calculation unit 74 (or by the reference interface determination unit 80 and the data calculation unit 74), whereon the gate 35 is set by the data calculation unit 74 (or by the reference interface determination unit 80 and the data calculation unit 74) to perform inspection (measurement) of the joint portion at the data calculation unit 74. In this manner, even if the interfaces between the solders 31 and the substrate-side pads 28 on the substrate 27 are not located stably due to variation caused by a tolerance in the thickness of the interposer 29 or the like, inspection (measurement) of measured portions can be performed at the data calculation unit 74 only with measurement as from the trigger position, and highly accurate ultrasonic measurement becomes possible.

Specifically, since the measurement object is the semiconductor package 26 including a plurality of joint portions, i.e., electrode points, at which the substrate-side pads 28 and the interposer-side pads 30 are bonded with the solders 31, a trigger is detected at each electrode point by the data calculation unit 74 to make determination on the waveform of the solder joint portion by the data calculation unit 74, whereby defectiveness or non-defectiveness is determined by the determination unit 75.

As described above, according to the present invention, it is possible to reduce, more significantly than before, influences such as deviation in time-delay in measurement objects in which a plurality of interfaces cross the direction of ultrasonic irradiation, enabling highly accurate ultrasonic measurement. As shown with an alternate long and short dash line G in FIG. 2, an ultrasonic wave that passes a path from the resin mold 33 through the interposer 29 to the solder 31 will pass a total of three kinds of layers. If the reference interface is at an electrode portion, the resin mold 33 and the interposer 29 are not between the reference interface and the electrode portion, and the influence of the interface between the medium such as the water 25 and the resin mold 33 and the interface between the resin mold 33 and the interposer 29 is thus negligible; accordingly, it is possible to reduce influences of deviation in time-delay significantly.

Figure 6:
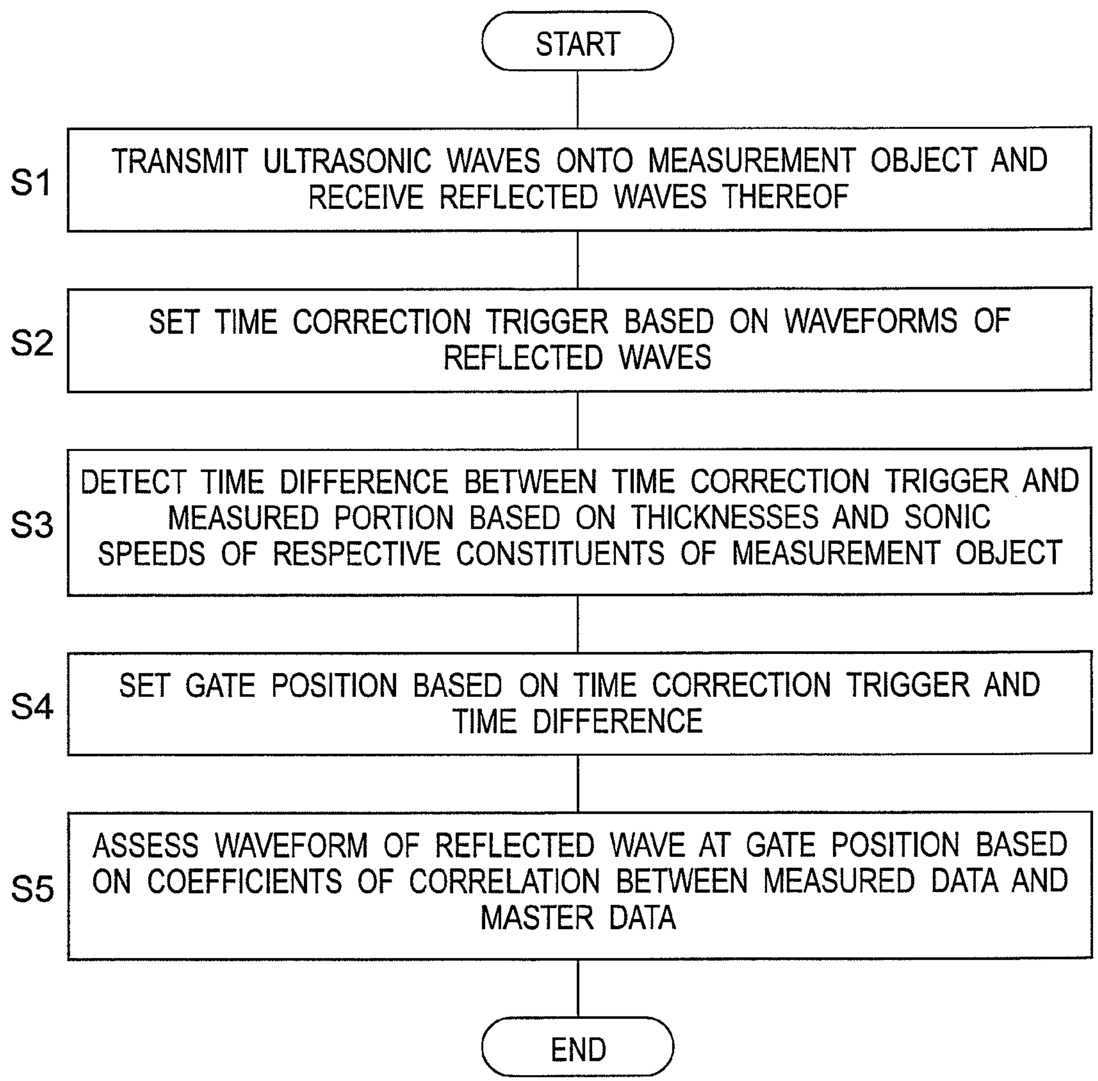
FIG. 6 is a flowchart of the operation of ultrasonic measurement according to the first embodiment.

A description is made on a flow of the first embodiment for a case of using a method other than the method in which comparison with master data is made in turn from a reference interface, with reference to FIG. 6.

FIG. 6 is a flow chart of the ultrasonic measurement according to the first embodiment.

In FIG. 6, first in step S1, ultrasonic waves are transmitted from the ultrasonic probe 21 onto a measurement object (the semiconductor package 26 in the first embodiment), and the reflected waves back from interfaces in the measurement object are received at the ultrasonic probe 21.

Subsequently, in step S2, a trigger (a time correction trigger) 34 is set by the data calculation unit 74 (or by the reference interface determination unit 80 and the data calculation unit 74), based on the waveforms of the plurality of reflected waves received at the ultrasonic probe 21 and the information of the interfaces on the basis of the structures of layers of the measurement object.

Then, in step S3, the time difference (the phase difference) between the trigger 34 and a measured portion (a joint portion between the solder 31 and the substrate 27 in the first embodiment) is detected by the data calculation unit 74, based on the thicknesses and sonic speeds of respective constituents of the measurement object.

Thereafter, in step S4, the position of a gate 35 (a measurement location) is set by the data calculation unit 74, based on the trigger 34 acquired at the data calculation unit 74 and the time difference (phase difference) on the basis of the structures of the layers.

Then, in step S5, the waveform of a reflected wave at the position of the gate 35 is evaluated by the data calculation unit 74 based on coefficients of correlation between the measured data and master data, which coefficients are found in turn from the trigger 34, whereby determination is made by the determination unit 75 as to whether or not the bonded condition of the measured portion is defective or not.

The above steps S1 to S5 are carried out over the entire surfaces of the measurement object (the semiconductor package 26), so that ultrasonic measurement and evaluation (determination of defectiveness or non-defectiveness) on the measurement object (the semiconductor package 26) can be made.

In the first embodiment, the portion that provides maximum amplitude intensity is set as a reference interface where difference in acoustic impedance is maximal. However, if the maximum amplitude intensity does not correspond to the reference interface due to such effect as noise, a portion other than the portion with maximum amplitude intensity may be set as a reference interface, in consideration of the above-mentioned factors.

According to the first embodiment, not a surface of a measurement object (e.g., an electronic component; more specifically, the semiconductor package 26) but a characteristic portion (an interface at an electrode joint portion or a portion close to the electrode joint portion, between layers of substances that are widely different from each other in acoustic impedance) inside the semiconductor package 26 is set as a trigger 34 by the data calculation unit 74 (or by the reference interface determination unit 80 and the data calculation unit 74), and a gate 35 is set by the data calculation unit 74 (or by the reference interface determination unit 80 and the data calculation unit 74) based on the trigger 34 to conduct inspection (measurement) of the joint portions at the data calculation unit 74. In this manner, even if the interfaces between the solders 31 and the substrate-side pads 28 on the substrate 27 are not located stably due to variation caused by a thickness tolerance of the interposer 29 or the like, inspection (measurement) of measured portions can be performed at the data calculation unit 74 only with measurement as from the trigger position, and highly accurate ultrasonic measurement becomes possible. Thus, it is possible to provide the highly accurate method and apparatus for ultrasonic measurement even for measurement objects in which a plurality of interfaces cross the direction of ultrasonic irradiation. In addition, it is possible to provide the electronic component manufacturing method of manufacturing, as products, electronic components that have been measured and evaluated as being non-defective through the above-described ultrasonic measuring method, as well as to provide the semiconductor packages for use in the ultrasonic measuring method. In particular, in the first embodiment, in order to solve the conventional issues with ultrasonic measuring methods, a unique way of taking a reference surface (a reference interface) is contrived to solve the conventional issues, wherein the reference surface is fabricated for use, in the course of the method of manufacturing a semiconductor package or a substrate, thereby allowing for improvement in ultrasonic measuring methods.

Second Embodiment

Figure 7:
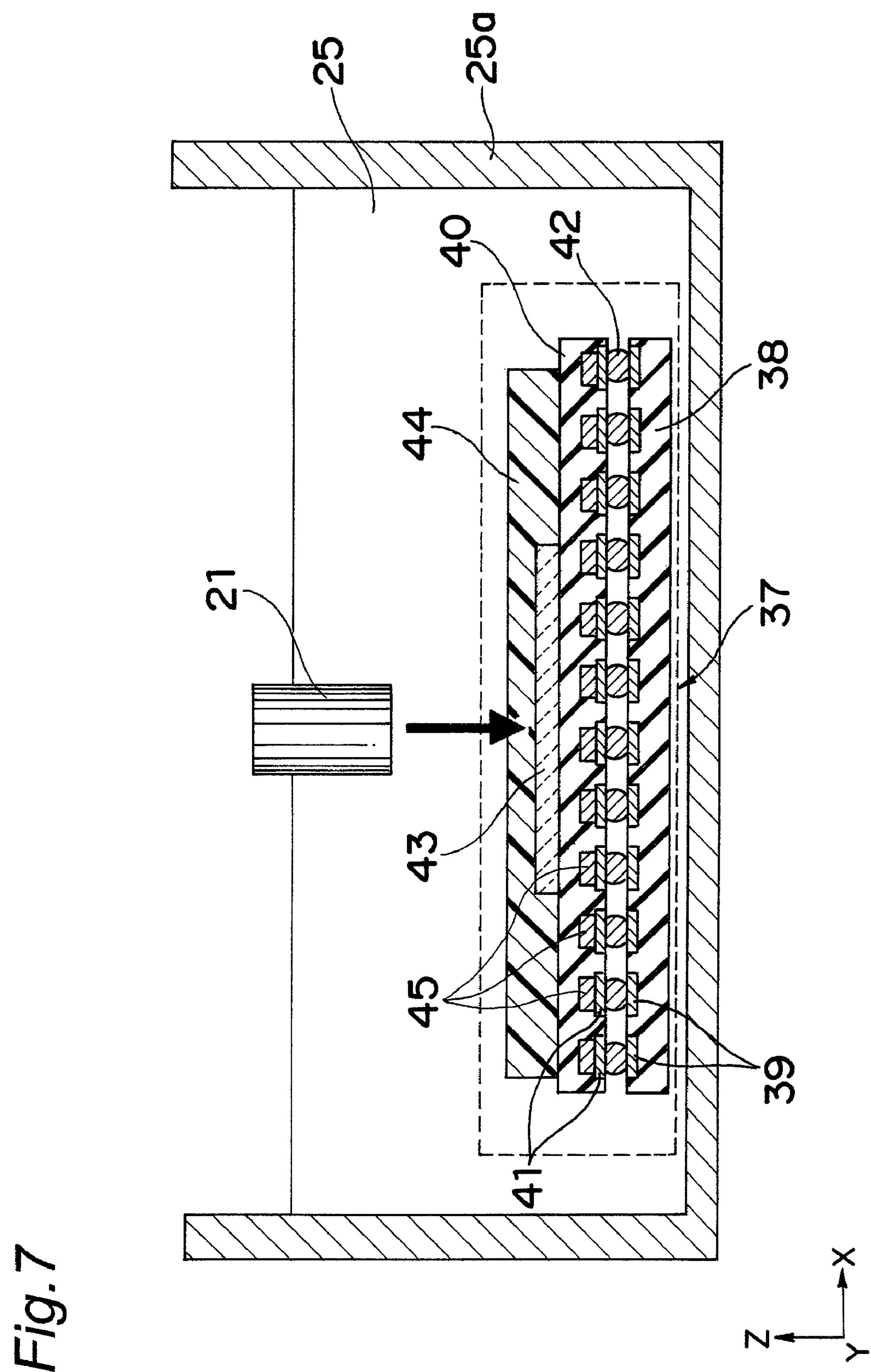
FIG. 7 is an explanatory view showing an operation of an ultrasonic measurement according to a second embodiment of the present invention.

FIG. 7 is an explanatory view showing an operation of ultrasonic measurement according to a second embodiment of the present invention.

In FIG. 7, a semiconductor package 37 serving as another example of the measurement object is constructed by, e.g., a substrate 38, substrate-side pads 39 provided on the upper surface of the substrate 38, an interposer 40 bonded to the substrate 38, interposer-side pads 41 provided on the lower surface of the interposer 40, solders 42 serving as an example of the bonding members for bonding the substrate-side pads 39 with the interposer-side pads 41, a semiconductor chip 43 directly connected with the interposer 40 through flip chip connection (not shown) or the like, a resin mold 44 covering the semiconductor chip 43, and marks 45 located at positions contacting the interposer-side pads 41 inside the interposer 40. The semiconductor package 37 is different from the semiconductor package 26 of the first embodiment in that the marks 45 are provided.

Such a semiconductor package 37 is manufactured in the following manner.

First, the interposer 40 is prepared, which interposer 40 has a number of interposer-side pads 41 on its lower surface with the marks 45 being deposited at positions contacting the interposer-side pads 41 inside the interposer 40.

Then, the semiconductor chip 43 is connected to the upper surface of the interposer 40 by means of flip chip connection or the like.

Then, the semiconductor chip 43 on the interposer 40 is covered with an insulating synthetic resin to form the resin mold 44.

After that, the solder 42 is provided either on each interposer-side pad 41 on the interposer 40 or each substrate-side pad 39 on the substrate 38.

Then, the interposer-side pads 41 are each connected with the substrate-side pads 39 on the substrate 38 with the solders 42 placed therebetween.

By manufacturing in this way, interfaces capable of functioning as a reference interface (a reference surface for determining defectiveness or non-defectiveness of a joint portion) are formed as the marks 45 at the time of manufacturing. That is, the reference interface from which waveform signals of ultrasonic waves reflected upon being irradiated can be acquired is formed, as the marks 45, of thin layers of a metal such as gold, at positions contacting the interposer-side pads 41 inside the interposer 40 in the semiconductor package 37. The metal layers provided as the marks 45 may be made of a material that has difference in acoustic impedance from that of the interposer 40. In the case where a glass epoxy is used for the interposer 40, the acoustic impedance is in the range of 2.9 to 3.6; therefore, e.g., copper (with acoustic impedance of 41.8), silver (with acoustic impedance of 37.8), Au (with acoustic impedance of 62.5), or the like may be used as a material of the marks 45, in consideration of the inherent acoustic impedances of the substances.

An epoxy resin is used as a material of the substrate 38, and copper (Cu) is used as a material of the substrate-side pads 39 and a material of the interposer-side pads 41. An epoxy resin is used as a material of the interposer 40. Materials of the solder 42 include a solder alloy such as Sn/Pb/Cu or Sn/Pb/Ag or a lead-free solder such as Sn/Ag/Cu or Sn/Cu. Si is used as a material of the semiconductor chip 43. A mixture of an epoxy resin and a filler ($SiO_2$) is used as a material of the resin mold 44. Gold (Au) is used as a material of the marks 45.

Used as the semiconductor package 37 of the second embodiment, for example, is a CSP package in which the package size and the silicon size are the same.

The marks 45 needs to have a thinnest possible size so as to reduce, even if variation in thickness of the marks occurs on the electrodes (pads) 41, effects caused therefrom. According to an example of the method of forming the marks 45, the marks 45 may be fabricated by vacuum evaporation or the like prior to fabrication of the electrode pads 41. More specifically, a metal mask with openings for forming the marks 45 is set on the interposer 40, and gold or the like is evaporated on the interposer 40, thereby forming the marks 45. The marks 45 may be arranged on all the interposer-side pads 41 or on the interposer-side pads 41 excluding part thereof. For example, as in FIG. 7, in the case where there are paths from the resin mold 44 past the interposer 40 to the solders 42 and paths from the resin mold 44 past the Si chip 43 and the interposer 40 to the solders 42, and if the results of measurement are not so different among the electrodes on the same paths, the marks 45 have only to be formed on pads 41 at two positions in some cases. Since, however, there is in fact variation in thickness and the like even on the same paths, measurement can be carried out at a higher level of accuracy when the marks 45 are provided on each of the electrodes. The maximum size of the marks 45 is equal to the size of the pads 41, and the minimum size is preferably the spot size of the ultrasonic waves (50 μm (110 MHz) to 150 μm (10 MHz), depending on the frequency). With regards to formation of the marks 45, the bigger, the more difficult is to form them. The marks 45 allow trigger positions to be set easily and conveniently, enabling ultrasonic measurement with reduced influence of the variation.

In the following, an ultrasonic measuring method according to the second embodiment is described.

As in the first embodiment, ultrasonic waves are transmitted from and received at the ultrasonic probe 21 through the medium of water 25.

Then, a measured portion (a joint portion between the solder 42 and the substrate 38) is evaluated based on the waveforms acquired at the ultrasonic probe 21, whilst, unlike the first embodiment, in the second embodiment, a reflected wave from a mark 45 serving as another example of the reference interface is used as a trigger by the data calculation unit 74. Information on the marks 45 (e.g., information that the marks 45 are provided on the semiconductor package 37 or information including the dimensions, arranged positions, and acoustic impedance value of the marks 45) is stored on the measurement position data memory 77.

In the second embodiment, as gold (Au) is used for the marks 45, the difference in acoustic impedance (the difference in acoustic impedance between the marks 45 and the interposer-side pads 41) is 62.5. In this case, the difference in acoustic impedance between the marks 45 and the interposer-side pads 41 is larger than the difference between the interposer-side pads 30 and the interposer 29 in the first embodiment, and a trigger can be set even more easily by the data calculation unit 74.

As described above, in the second embodiment, the marks 45 are buried in the semiconductor package 37 (made into buried objects) and the material of the marks 45 or the material of the interposer 40 is freely decided, so that the difference in acoustic impedance can be adjusted, and that a trigger with a large difference in acoustic impedance can be generated.

Figure 8A:
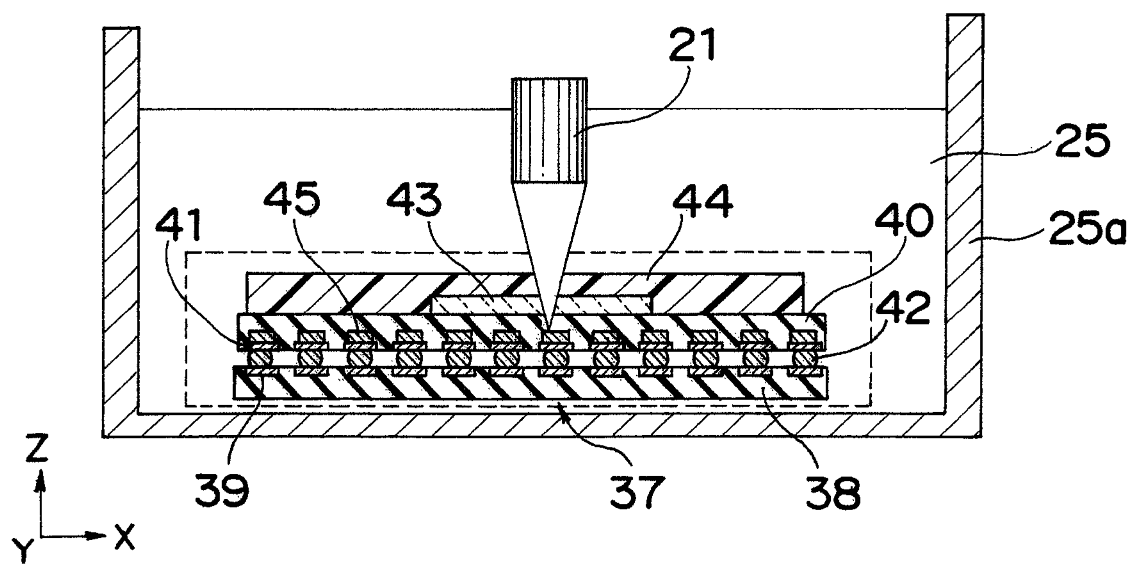
FIG. 8A is an explanatory view showing the operation of ultrasonic measurement at time t=0 according to the second embodiment.
Figure 8B:
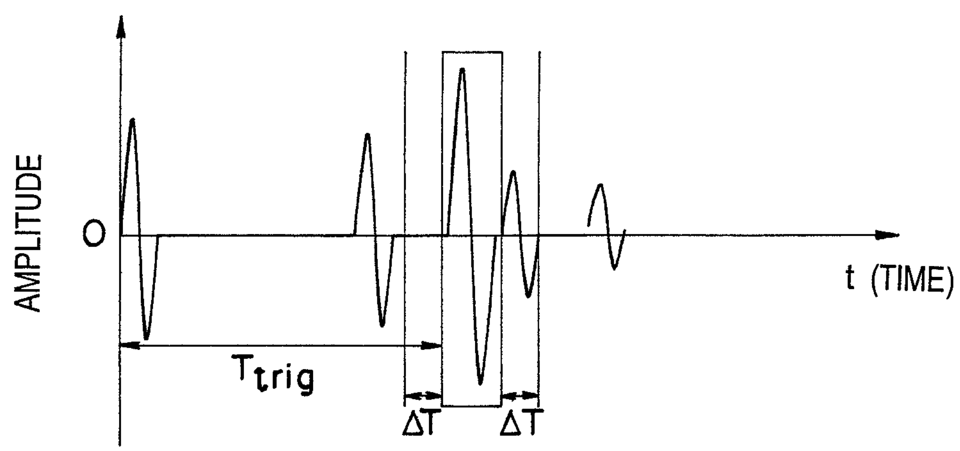
FIG. 8B is a view illustrating a waveform in the operation of the ultrasonic measurement at time t=0 according to the second embodiment (the vertical axis indicates the value of coefficient of correlation and the transverse axis indicates the time)
Figure 9A:
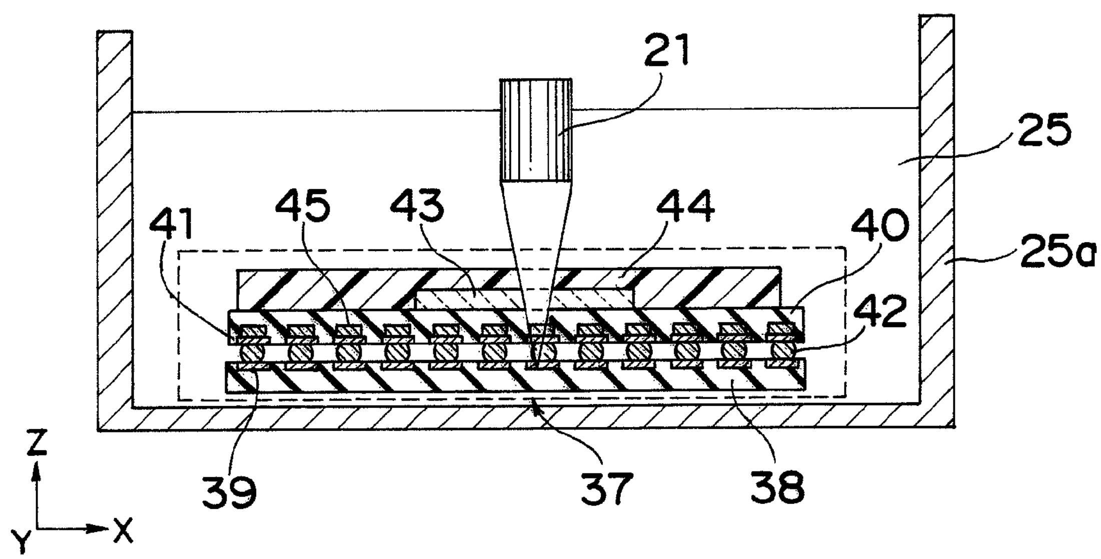
FIG. 9A is an explanatory view showing the operation of ultrasonic measurement at time t=1 according to the second embodiment.
Figure 9B:
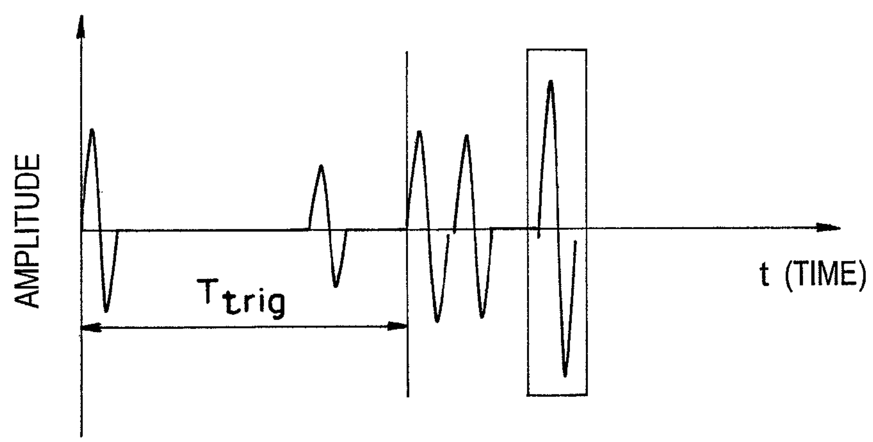
FIG. 9B is a view illustrating a waveform in the operation of the ultrasonic measurement at time t=1 according to the second embodiment (the vertical axis indicates the value of coefficient of correlation and the transverse axis indicates the time)

FIG. 8A is an explanatory view showing the operation of ultrasonic measurement at time t=0 according to the second embodiment, and FIG. 8B is a view illustrating a waveform generated in the operation of the ultrasonic measurement at time t=0 according to the second embodiment. FIG. 9A is an explanatory view showing the operation of ultrasonic measurement at time t=1 according to the second embodiment, and FIG. 9B is a view illustrating a waveform generated in the operation of the ultrasonic measurement at time t=1 according to the second embodiment.

As shown in FIGS. 8A and 8B, a description is made here on an example directed to the structure in which the marks 45 are buried in the semiconductor package 37. First, a focal point is set on an interface of a mark 45, based on which the position of the focal point is further adjusted so as to observe a target interface of the solder.

First, it is considered that ultrasonic waves from the ultrasonic probe 21 are focused on a joint portion between the interposer 40 and the mark 45, using the ultrasonic probe drive unit 21*a*. As has been described earlier, time $T_{trig}$ at which a reflected wave is generated on the interface between the interposer 40 and the mark 45 is calculated and found in advance at the data calculation unit 74 based on the thicknesses and sonic speeds of constituents of the semiconductor package 37. $T_{trig}$ corresponds to a period wherein the reflected waveform on a surface of the resin mold 44 is set at time t=0. In the second embodiment, since there is a tolerance (variation in thickness) between the interposer 40 and the proximate silicon of the semiconductor chip 43, a focal distance that provides the maximum waveform within a section $T_{trig}\pm\Delta T$ including a minimal period $\Delta T$ therearound is sought for.

As shown in FIG. 8B, since the reflected wave on the interface between the interposer 40 and the mark 45, which reflected wave serves as a trigger, has a larger intensity value than the reflected waves on other interfaces, the waveform itself is easily measured. In the present example, in order to search for a position at which the trigger has the maximum signal intensity, the ultrasonic probe 21 is moved toward the semiconductor package (to the lower side of the paper plane of FIG. 8A) by the ultrasonic probe drive unit 21*a*. After that, the value of a focal distance $D_{trig}$ by which the waveform intensity of the trigger becomes maximal is stored on the internal memory of the data calculation unit 74.

Subsequently, as shown in FIG. 9A, the focal point of the ultrasonic probe 21 is set on the solder 42 and a substrate-side pad 39 by the ultrasonic probe drive unit 21*a*. The lowered distance $\Delta D$ from the focal distance $D_{trig}$ is found by measuring in advance a semiconductor package of the same kind (i.e., made of the same material), at the data calculation unit 74.

As shown in FIG. 9B, the lowered distance $\Delta D$ is found by calculating at the data calculation unit 74 an arrival time of the ultrasonic waves from the focal distance $D_{trig}$ based on the thickness and sonic speed of the solder 41 and specifying the temporal position at the data calculation unit 74.

Then, the ultrasonic probe 21 is lowered toward the semiconductor package (to the lower side of the paper plane of FIG. 9A) until the waveform of a joint portion between the solder 42 and the substrate 38 comes to have maximum intensity. $\Delta D$ is a distance lowered from the focal distance $D_{trig}$; in actual measurement, the lowered distance $\Delta D$ is found in only initial measurement, and in measurement thereafter, a focused state can be brought about through adjustment by the ultrasonic probe drive unit 21*a* based on the focal distance $D_{trig}$.

Through this system, it becomes possible to correct variation in focal position caused by a thickness tolerance (variation in thickness) of the semiconductor package 37.

Third Embodiment

Figure 10:
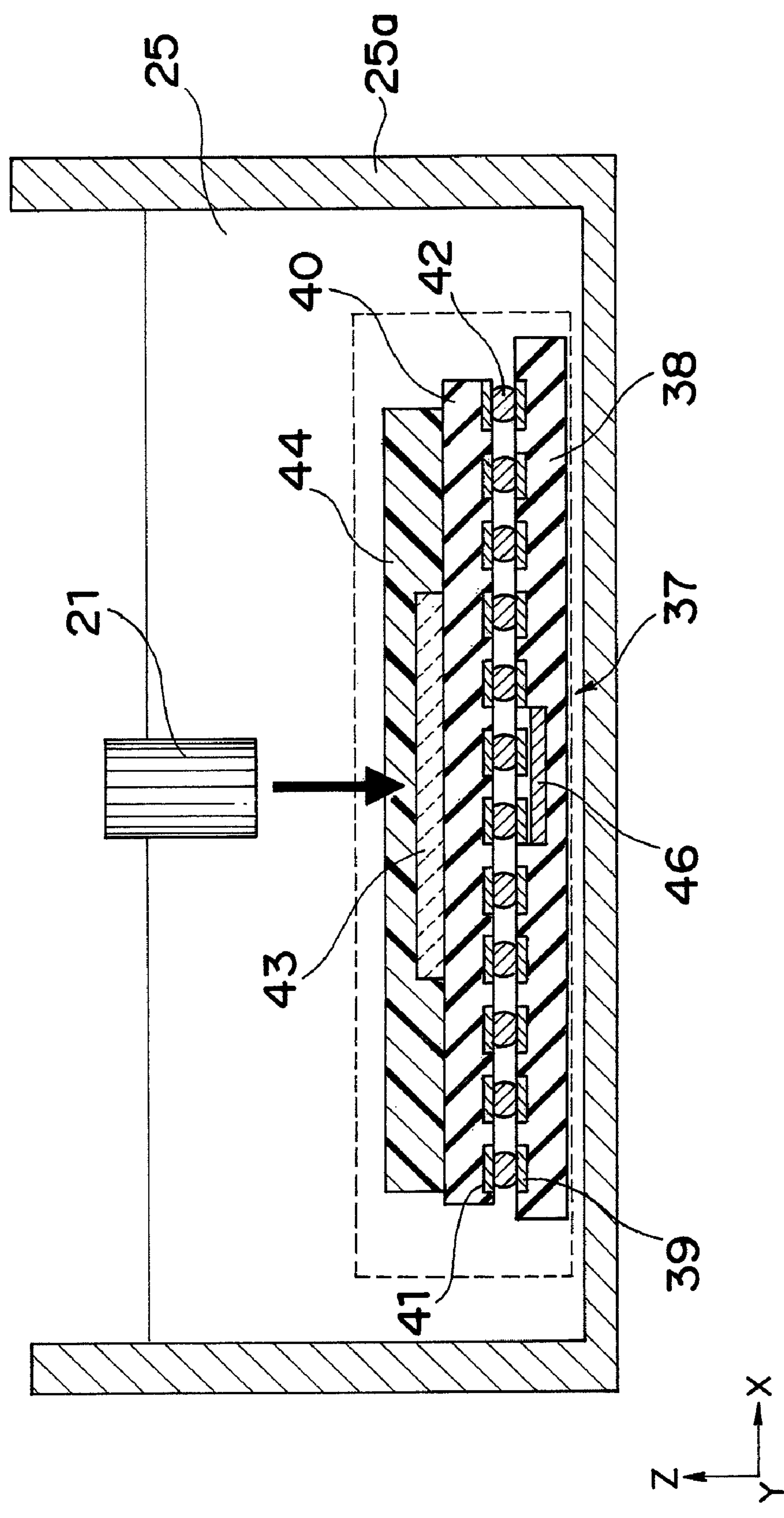
FIG. 10 is a view illustrating another mode of the operation of ultrasonic measurement according to the second embodiment.
Figure 11:
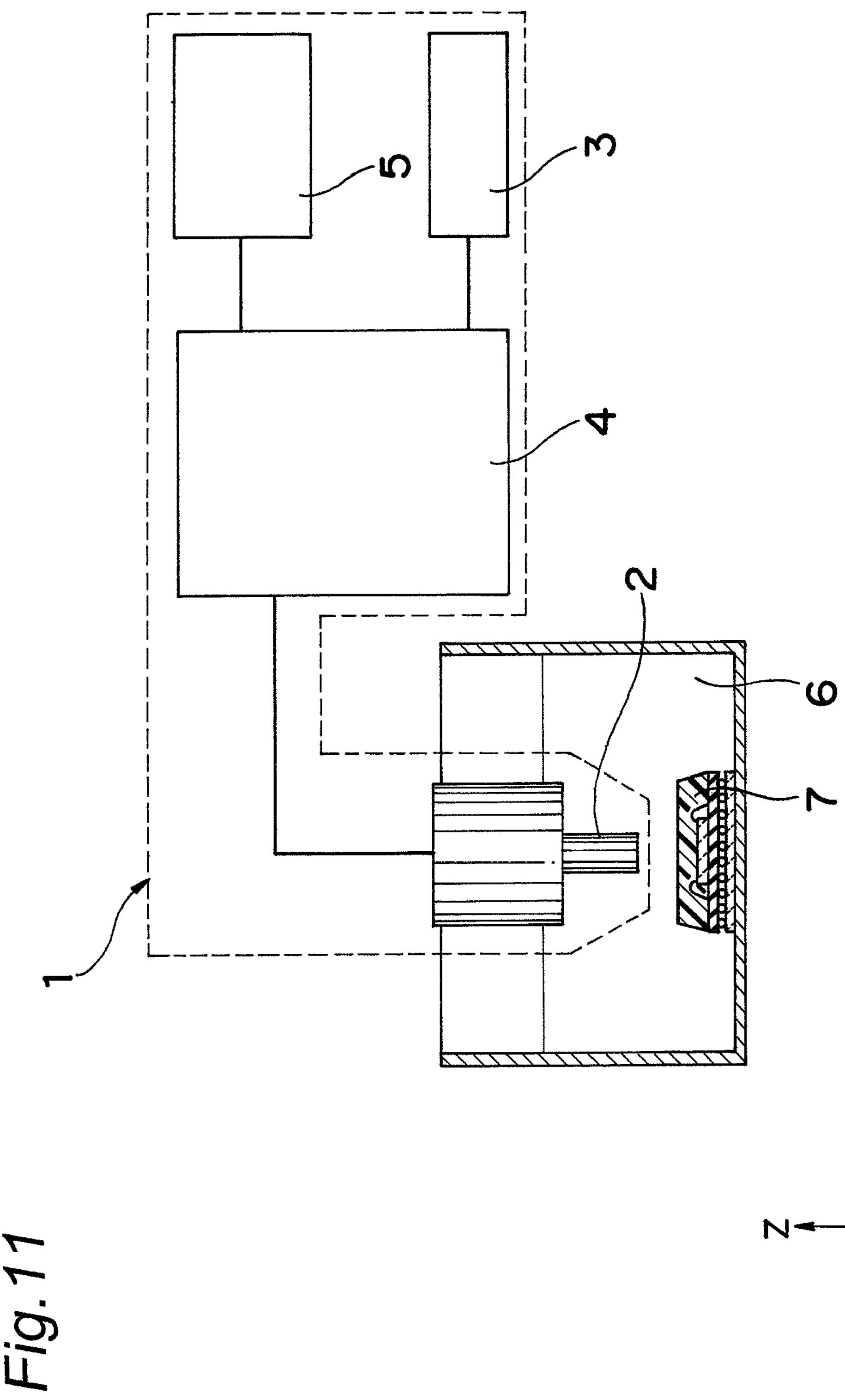
FIG. 11 is a basic structural view of a conventional ultrasonic measuring method.
Figure 12:
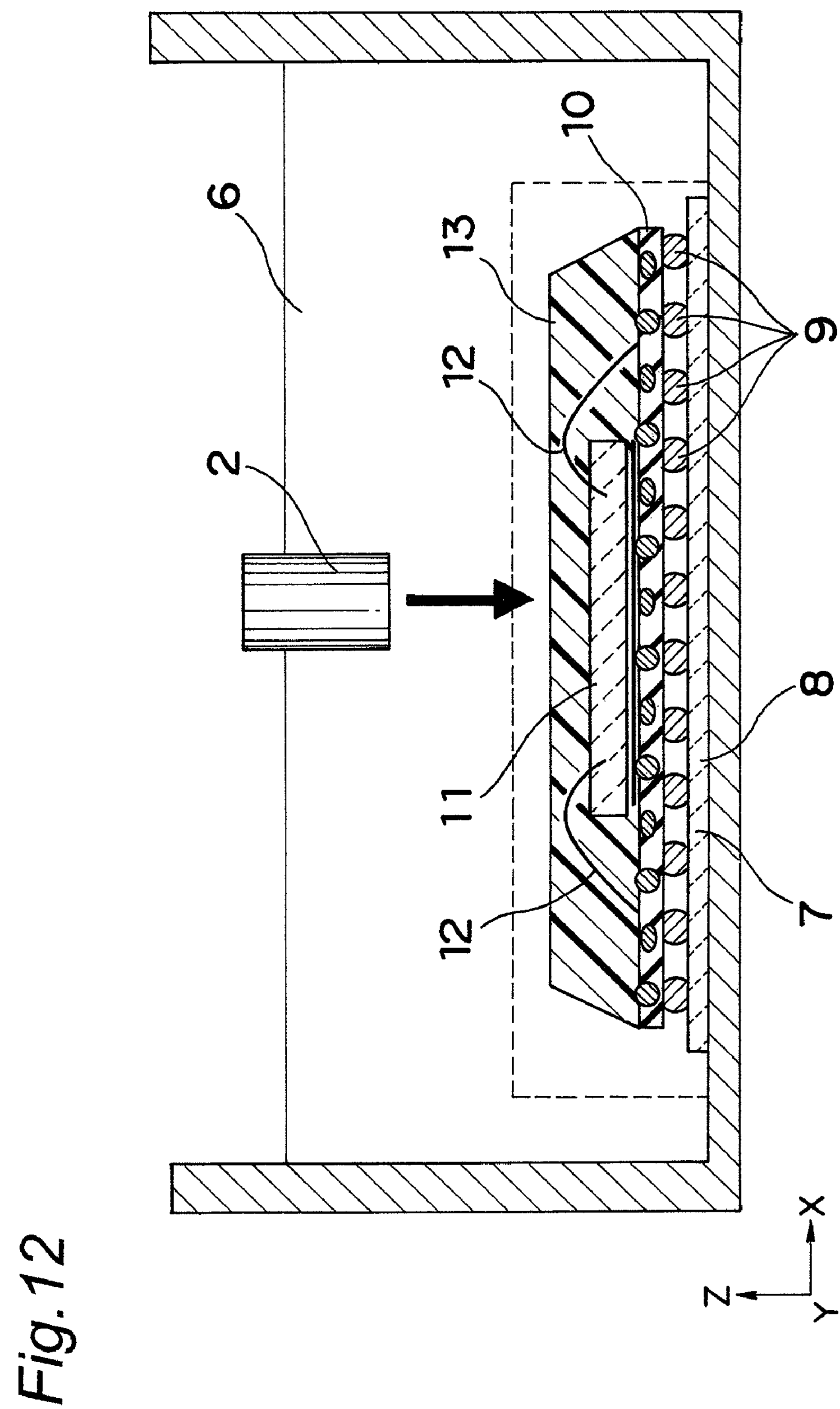
FIG. 12 is a schematic view of the conventional ultrasonic measurement.
Figure 13:
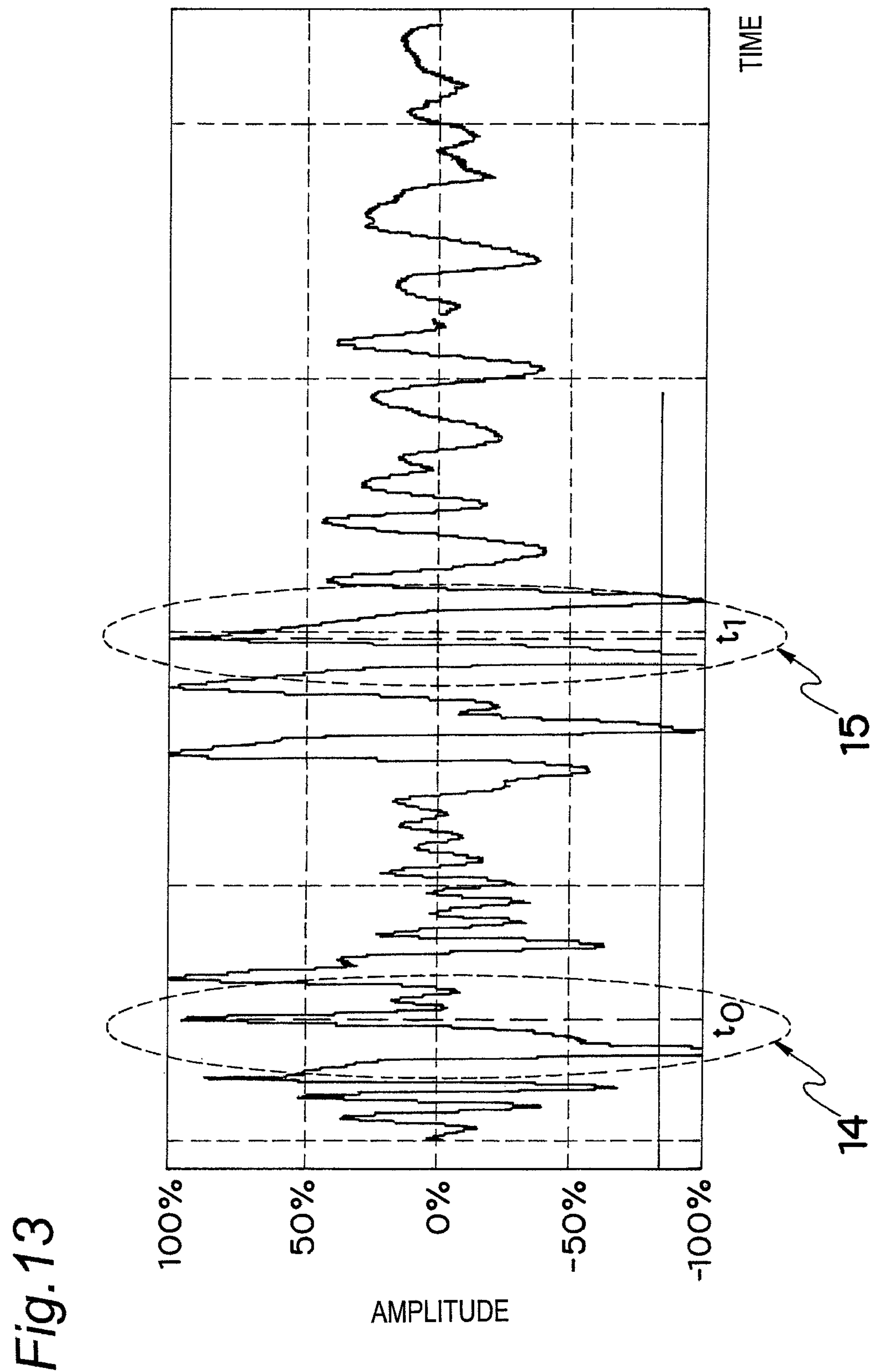
FIG. 13 is a view illustrating an ultrasonic waveform acquired in the conventional ultrasonic measurement.
Figure 14:
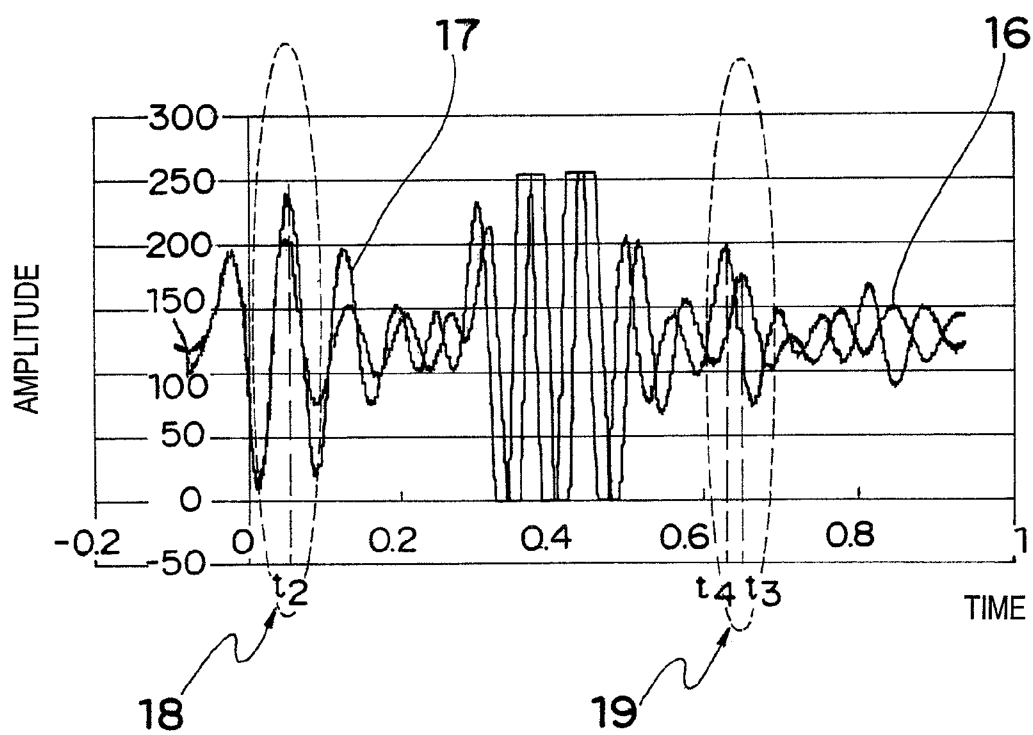
FIG. 14 is a view illustrating waveforms of ultrasonic reflected waves according to the conventional ultrasonic measurement.

FIG. 10 is a view illustrating an operation of ultrasonic measurement according to a third embodiment of the present invention.

In FIG. 10, the third embodiment is different from the second embodiment (FIG. 7) in that, in the third embodiment, a mark 46 is provided in the substrate 38 instead of the marks 45 in the interposer 40 of the second embodiment, the mark 46 serving as another example of the reference interface. Since, in the present embodiment, below (at the lower side of the paper plane of FIG. 10) the substrate 38 is not a layer, the material of the mark 46 may be one totally reflective of ultrasonic waves, and the mark 46 may be, e.g., an airgap layer. Alternatively, the material of the substrate 38 may be changed to widen the difference in acoustic impedance between the material of the substrate 38 and the material of the substrate-side pads 39, thereby increasing the reflective intensity of the ultrasonic waves. In this case, an interface between the material of the substrate 38 and the material of the substrate-side pads 39 serves as another example of the reference interface.

Fourth Embodiment

In a fourth embodiment of the present invention, a description is made on a method wherein any one of the foregoing first to third embodiments is applied so as to use the trigger for focal positioning of the ultrasonic probe 21 in an ultrasonic flaw detection of detecting an internal flaw of a measurement object (a semiconductor package).

A focusing probe is frequently used in ultrasonic flaw detection, and focal positioning relative to a measurement object (a semiconductor package) assumes great importance for this reason. As has been described earlier, since there is variation (a tolerance) in thickness in semiconductor packages, even when a focal position is set in advance, a semiconductor package to be actually measured shall have an error in proportion to its thickness. In the fourth embodiment, the trigger is used to perform focal positioning for each semiconductor package.

Ultrasonic flaw detection is performed after such focal positioning, so that inspection with improved accuracy can be effected.

While the foregoing embodiments of the present invention are characterized by analysis of amplitude intensity signals of ultrasonic reflected waves, the method of the fourth embodiment can probably be applied also to another means based on, e.g., a transmission method in the case where the basic technique, issue, and solution are the same and an object having a similar structure is measured.

It should be noted that the present invention is not limited to the foregoing embodiments, and the present invention may obviously be changed in various ways without departing from the subject matter of the present invention.

For example, the materials of the pads may be copper, gold, silver, or the like.

Also, as shown in the conventional example, if the electronic component has lead wires and the lead wires hampers measurement operation, the reference interface may be set in an area other than the areas where ultrasonic waves may be blocked or interrupted by the lead wires.

The ultrasonic measuring method according to the present invention is applicable to such use as nondestructive inspection and the like of semiconductor packages in which a plurality of interfaces are laminated inside and cross the direction of ultrasonic irradiation. In addition, the electronic component manufacturing method and the semiconductor package according to the present invention are applicable to electronic component manufacturing methods of manufacturing, as products, electronic components that have been measured and evaluated as being non-defective by the ultrasonic measuring method, as well as to semiconductor packages measurable with the ultrasonic measuring method.

By properly combining the arbitrary embodiments of the aforementioned various embodiments, the effects possessed by the embodiments can be produced.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An ultrasonic measuring method comprising:

receiving, at an ultrasonic probe, waveform signals of ultrasonic waves transmitted from the ultrasonic probe and reflected from a plurality of interfaces in a measurement object;

detecting, by a calculation unit, a waveform signal of a reflected wave on a reference interface in the measurement object based on amplitudes of the waveform signals received at the ultrasonic probe;

adjusting a position of the ultrasonic probe, based on a received waveform signal, with the ultrasonic probe and the measurement object being moved toward each other; and measuring, by the calculation unit, an interface to be measured of the measurement object, the interface to be measured being specified with the waveform signal of the reflected wave on the reference interface set as an origin, wherein the adjusting the position of the ultrasonic probe is performed after the detecting the waveform signal and before the measuring the interface to be measured of the measurement object.

2. The ultrasonic measuring method according to claim 1, wherein the measurement object is an electronic component, wherein the interface to be measured is a portion inside the electronic component, the portion being at an electrode joint portion or a portion adjacent to the electrode joint portion at which electrodes are bonded with a bonding member, and wherein the interface to be measured is measured by the calculation unit, and a bonded condition of the electrode joint portion at the interface to be measured is evaluated by the calculation unit.

3. The ultrasonic measuring method according to claim 1, wherein, in the detecting the waveform signal, the reference interface is an interface that provides a maximum amplitude intensity among the plurality of interfaces in the measurement object.

4. The ultrasonic measuring method according to claim 1, wherein, in the detecting the waveform signal, the reference interface is a surface of a buried object buried in the measurement object.

5. The ultrasonic measuring method according to claim 1, wherein, in the detecting the waveform signal, (i) the measurement object is a semiconductor package, and (ii) the reference interface is a portion inside the semiconductor package, the portion being (a) at an electrode joint portion or a portion adjacent to the electrode joint portion at which the electrodes are bonded with a bonding member, and (b) located at an interface between two layers of different materials.

6. The ultrasonic measuring method according to claim 1, wherein, in the measuring the interface to be measured of the measurement object, (i) a waveform signal detected after the waveform signal of the reflected wave on the reference interface is compared with a preliminarily inputted waveform signal of a non-defective product with reference to the waveform signal of the reflected wave on the reference interface, and (ii) the interface to be measured is evaluated based on result of the comparison.

7. An electronic component manufacturing method comprising:

measuring and evaluating an interface to be measured of an electronic component according to the ultrasonic measuring method defined in claim 1, the measurement object being the electronic component; and providing, as a product, the electronic component evaluated as being non-defective.

* * * * *